(12) United States Patent
Galvão

(10) Patent No.: US 11,612,672 B2
(45) Date of Patent: Mar. 28, 2023

(54) WIRELESS ELECTROMECHANICAL DEVICE FOR DEMONSTRATING MULTIPLE FRAGRANCES OR AROMAS

(71) Applicants: PANAPANAS INC. LTD, Nassau (BS); Cláudia Galvão, São Paulo (BR)

(72) Inventor: Cláudia Galvão, São Paulo (BR)

( * ) Notice: Subject to any disclaimer, the term of this patent is extended or adjusted under 35 U.S.C. 154(b) by 651 days.

(21) Appl. No.: 16/702,771

(22) Filed: Dec. 4, 2019

(65) Prior Publication Data

US 2021/0170060 A1    Jun. 10, 2021

(51) Int. Cl.

| | | |
|---|---|---|
| *A61L 9/12* | (2006.01) | |
| *B05B 7/24* | (2006.01) | |
| *B05B 11/00* | (2006.01) | |
| *B05B 12/08* | (2006.01) | |

(52) U.S. Cl.
CPC ............ *A61L 9/125* (2013.01); *B05B 7/2491* (2013.01); *B05B 7/2497* (2013.01); *B05B 11/0054* (2013.01); *B05B 11/0078* (2013.01); *B05B 12/08* (2013.01); *A61L 2209/111* (2013.01); *A61L 2209/133* (2013.01); *A61L 2209/134* (2013.01)

(58) Field of Classification Search
CPC ............ A61L 9/125; A61L 2209/111; A61L 2209/133; A61L 2209/134; B05B 7/2491; B05B 7/2497; B05B 11/0054; B05B 11/0078; B05B 12/08
See application file for complete search history.

(56) References Cited

U.S. PATENT DOCUMENTS

| | | |
|---|---|---|
| 5,167,877 A | 12/1992 | Pai |
| 2003/0091464 A1 | 5/2003 | Richards |
| 2003/0091466 A1 | 5/2003 | Benko et al. |
| 2004/0241053 A1 | 12/2004 | Thompson et al. |
| 2006/0153731 A1 | 7/2006 | Brown et al. |

FOREIGN PATENT DOCUMENTS

WO    0209776 A2    2/2002

*Primary Examiner* — Sean E Conley
(74) *Attorney, Agent, or Firm* — Piloff Passino & Cosenza LLP; Sean A. Passino; Rachel K. Pilloff

(57) ABSTRACT

Includes an electromechanical device (1), which acts like an electronic catalog for the olfactory testing of different fragrances or aromas, contained in an absorbent cylindrical element (2) inserted into individual cartridges (3), which are interchangeable and encased in a carousel (4), supported on central bearings (5) and radially moved by means of an electric motor (6) with reducer (7) and gearing (8) that acts in a circular rack (9). Upon receiving a command, via application, the carousel (4) turns positioning the cartridge (3), corresponding to the fragrance or aroma chosen, in front of the connector nozzle (10), thanks to a positioning sensor (S), which counts the turns of the shaft of the electric motor (6). Next, a mechanical actuator (11) formed by an electric motor (12), gearing (13) that acts in a straight rack (14), which in turn drives a drawing cane (15), which pushes, and then retracts the cartridge, (3) inside the connector nozzle (10), and jointly with the air flow coming from a flexible hose (16), from where the air inflated by a compressor (17) enters said cartridge (3), forces the emission of the scent by the outlet orifice (18) of the top (19) of the box (20), thus providing the user a reliable olfactory testing.

15 Claims, 26 Drawing Sheets

WIRELESS ELECTROMECHANICAL DEVICE FOR DEMONSTRATING MULTIPLE FRAGRANCES OR AROMAS

FIELD

The present description pertains to the segment of demonstrating and testing fragrances or aromas, and refers to an unprecedented device, which acts like an electromechanical catalog, capable of containing from one to 100 (a hundred) types of fragrances or aromas. When connected to a wired or wireless computerized system, which will command it by means of an application, this device will be capable of finding the selected fragrance in a carousel, and then carrying out a controlled burst of the air aromatized by the fragrance contained in the cartridge duly positioned in the carousel per se, providing the user a reliable olfactory experience, since it uses the concept of "dry scent", since in the exhalation system there is no heating, which would mischaracterize the fragrance by the evaporation of the more volatile notes. If the user wishes to try another fragrance or aroma, he/she simply chooses it in the application, and the apparatus will select the fragrance chosen.

BACKGROUND

The current state of the art anticipates some patent documents related to testing devices for fragrances and aromas, such as U.S. Pat. No. 5,167,877A entitled "Air purifier with perfume dispensing control"—used in the air purifying sector, the equipment described releases different perfumes, through the passage of air coming from a pump, for the cartridge of previously-selected perfume and consequent outlet of the perfume into the environment. It uses a solenoid air pump and carousel driven by electromagnet.

The apparatus above does not have a friendly interface with the user due to the lack of electronics, which would enable commands by means of applications and control of the intensity and scope of perfume emission.

Mechanically, the prior art presents constructive complexity, as it is made up of many components, besides requiring a considerably powerful solenoid pump, in view of the fact that the air is pumped into a liquid medium (perfume) to produce bubbles and thus bring the aroma to the outlet orifice. It has been proven that systems using bubbling to draw the aroma do not provide a good olfactory experience.

Still mechanically speaking, the prior art has a rotary table driven by electromagnet, whereas the return to the starting point occurs by means of springs. The mechanism is imprecise and is subject to wear and tear, for example, in the springs which will increase the imprecision or will mal function when their elasticity is lost.

Lastly, the constructive complexity and the excess of components may cause defects due to handling during demonstration, besides making its size rather voluminous.

US 2004/0241053 A1, entitled "Apparatus for dispensing volatile material into the environment"—used in the air aromatization sector. The equipment consists of a set of elements, with perfume disposed on a rotary disk, such that when positioning the chosen element an air flow generated by a blower traverses the element, loading the perfume into the environment. The document cites a perfume heating element to facilitate volatilization. The disk positioning system is electronic and controlled by sensors, motors and electronic circuits.

It is known that heating perfumes distorts them as the more volatile notes are released first. Another drawback is that there is an excess of mechanical components such as: gearings, shafts, couplings, which result in an apparatus of considerable volume, besides hindering assembly and making the operation liable to defects or breakage of components.

WO02/09776 A2, entitled "System and methods for dispensing scents into the environment, and for providing scent-containing articles of manufacture"—the equipment described pertains to the sector of dispensing multiple volatile products into the environment, including perfumes. A disk receives various cartridges containing the volatile substances. An electronic system that can be commanded by a computer, or directly on the equipment, positions the chosen cartridge and by means of heating and passage of air coming from fan, the substance is released into the environment.

As in the previous document, the use of heating to release the fragrances, mischaracterizes the substances due to the premature evaporation of more volatile notes.

Objectives of Some Embodiments

It is an objective of some embodiments to propose an electromechanical device that acts as an electronic catalog for demonstrating multiple fragrances or aromas, wherein the chosen cartridge is mechanically moved to the emission position, and ventilated so that the air draws the scented vapors to the outlet orifice;

It is an objective of some embodiments to propose an electromechanical device, ecologically correct and sustainable, since it prevents on a monthly basis the consumption of tons of paper used in the traditional direct sales catalogs;

It is an objective of some embodiments to propose an electromechanical device for demonstrating multiple fragrances or aromas, which uses the concept of "dry scent", being activated by air ventilation, means the fragrances/aromas do not lose their original characteristics, since they did not undergo the action of elements liable to alter them, as occurs in the electro-thermal activation devices. It is known that heating the fragrance/aroma mischaracterizes its scent, since in the first heating, more volatile compounds (evaporating before others) are lost. A fragrance is composed of a great number of chemical substances, each having a different boiling point (evaporation). Normally, the scent exhaled by pulverization or evaporation is not absorbed appropriately and/or with precision by the human brain already on the fourth testing, according to studies carried out in the perfumery segment.

It is an objective of some embodiments to propose an electromechanical device for demonstrating multiple fragrances or aromas, whose concept of "dry scent" enables the testing, with precision and real aroma, various fragrances. In some of these embodiments it is possible to test twenty fragrances with distinction of the notes of the perfumes;

It is an objective of some embodiments to propose an electromechanical device for demonstrating multiple fragrances or aromas, which will be used as a digital catalog to present olfactory tests.

It is an objective of some embodiments to propose an electromechanical device for demonstrating multiple fragrances and aromas, capable of offering a multiple and controlled olfactory testing for the user.

It is an objective of some embodiments to propose an electromechanical device for demonstrating multiple fragrances and aromas, wherein the user using the apparatus connected to an electronic device with its application, may replace the kits of glass flasks, olfactory strips or, catalogs of samples and the equipment that use heating in the release of the scent and mischaracterize the fragrances.

It is an objective of some embodiments to propose an electromechanical device for demonstrating multiple fragrances and aromas, the working principle of which saves on fragrances and aromas, since the device does not pulverize, does not bubble, does not nebulize, nor does it heat the fragrances and aromas.

It is an objective of some embodiments to propose an electromechanical device for demonstrating multiple fragrances and aromas, which solves the drawbacks of other equipment, which contaminate the surfaces of the very emitting device, leaving it impregnated with the residual scent, adversely affecting the olfactory experience by the mixture of the scents. This device presents the advantage of the internal air flow of the system is impregnated only inside the cartridge, and released directly to the outlet orifice, eliminating the possibility of the mixture of the aromas or fragrances.

It is an objective of some embodiments to propose an electromechanical device for demonstrating multiple fragrances and aromas, which solves the drawbacks of other equipment, which store the scents when not in use, since it may optionally have an autoclean system which, after the use, conducts all the remaining scent outwardly of the device.

It is an objective of some embodiments to propose an electromechanical device for demonstrating multiple fragrances and aromas, capable of generating greater savings on fragrances or aromas, since there is no wastage with nebulization, bubbling or pulverization that require greater volumes. As already described, there are savings on glass flasks used for demonstrating perfumes, as well paper strips (olfactory strips).

It is an objective of some embodiments to propose an electromechanical device for demonstrating multiple fragrances and aromas, compact in size, similar to a tablet, which facilitates transport and handling, and with capacity for up to 100 (one hundred) types of fragrances/aromas.

It is an objective of some embodiments to propose an electromechanical device for demonstrating multiple fragrances and aromas, capable of generating a large number of bursts, for demonstrating and appreciating multiple fragrances and aromas, and which may replace the traditional glass flasks of samples of fragrances/aromas. This is possible due to the reduced volume inside the cartridges, associated to the ventilation of the concentrates of fragrances/aromas. The result is a satisfactory olfactory experience, in time, purity, intensity, reproducibility and durability of the cartridges, when compared to the current showcases.

It is an objective of some embodiments to propose an electromechanical device for demonstrating multiple fragrances and aromas that offers a satisfactory experience at a competitive cost, when compared with the current systems of samples in flasks and showcases.

It is an objective of some embodiments to propose an electromechanical device for demonstrating multiple fragrances and aromas, capable of being operated or controlled by various electronic interface means. Besides providing an application or program for making the selection and emission of the aromas, the system may also be driven by buttons in its box.

It is an objective of some embodiments to propose an electromechanical device for demonstrating multiple fragrances and aromas, having optimal cost/benefit ratio, since it presents a reduced number of components, with consequent drop in defects and facilitation of the manufacturing process, and quality control.

SUMMARY OF EMBODIMENTS

The electromechanical device for demonstrating multiple fragrances or aromas invented is nothing more than a compact electronic catalog capable of offering the user "dry" olfactory testing of different fragrances or aromas. The device in question is formed by a box with a movement mechanism that comprises a carousel, which accommodates up to one hundred cartridges containing fragrances or aromas, duly contained in an absorbent cylindrical element. On being triggered via application, the device means that the selected cartridge, housed in said carousel, turns, thanks to an electric motor with gearbox, up to the connector nozzle. By means of a mechanical actuator, driven by electric motor, gearing and rack, the cartridge is nudged inside the connector nozzle, at which time it receives an air flow coming from a compressor, which when traversing a flexible hose, forces the elastomeric projections that act as a valve of a path, thus occupying the cartridge and, spilling out only the gaseous portion of the fragrance to the upper outlet orifice of the cartridge per se, thus enabling a reliable olfactory testing. Therefore, when the cartridge is displaced forward, its top, which incorporates the valve of a path, displaces the pivoting handle which in turn releases a fragrance or aroma to the outlet orifice. Once testing has finished, the cartridge returns to the starting position. At this moment, the pivoting handle also returns closing the outlet orifice of the box and of the cartridge, which prevents the fragrances/aromas from mixing. Each fragrance or aroma is contained in a cartridge (refill), and these cartridges disposed in a carousel, and each cartridge may offer over 30 bursts (testings). The cartridges may be easily replaced, as they are encased in the carousel and accessible by way of a recharge window outside the casing.

BRIEF DESCRIPTION OF THE DRAWINGS

The embodiments will now be described in its embodiment, and for better understanding, references will be made to the accompanying drawings, representing the following.

DETAILED TECHNICAL DESCRIPTION OF EMBODIMENTS

Figure 1:
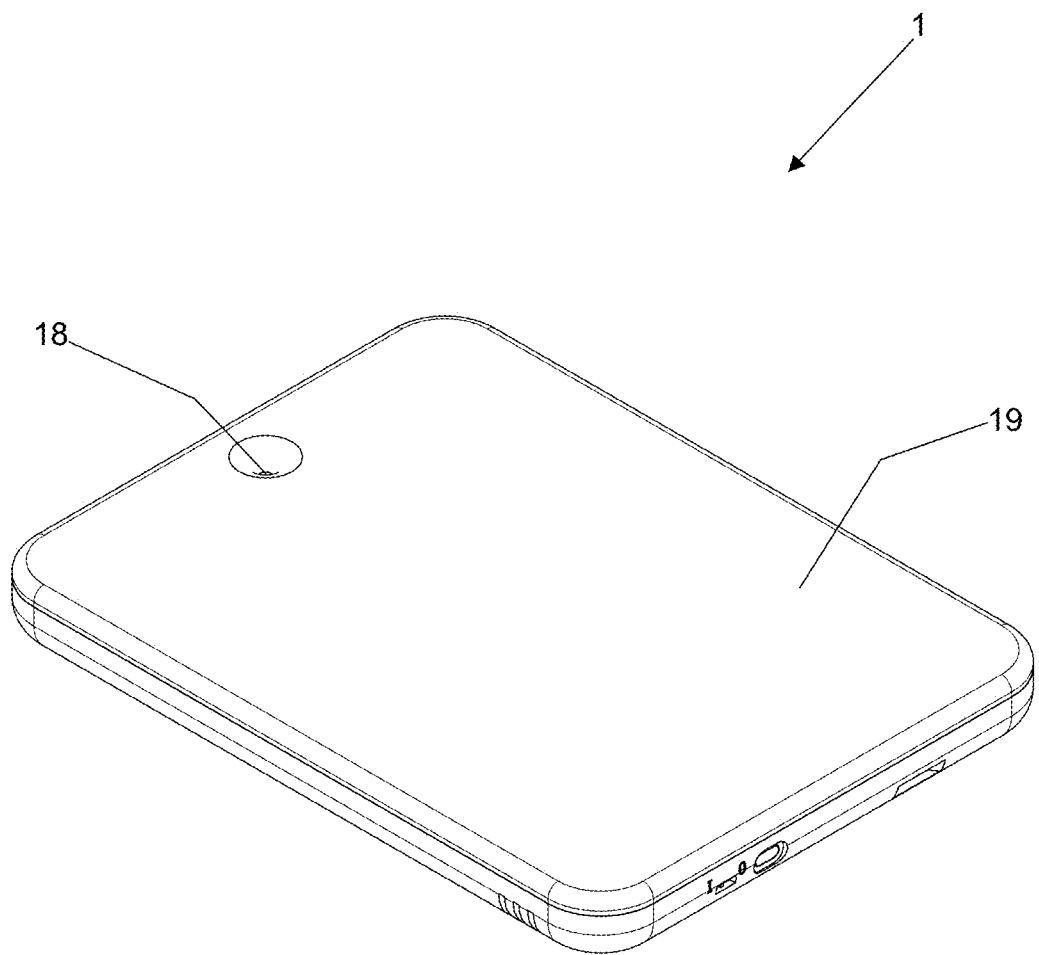
FIG. 1: A perspective view of the wireless electromechanical device for demonstrating multiple fragrances or aromas.
Figure 2:
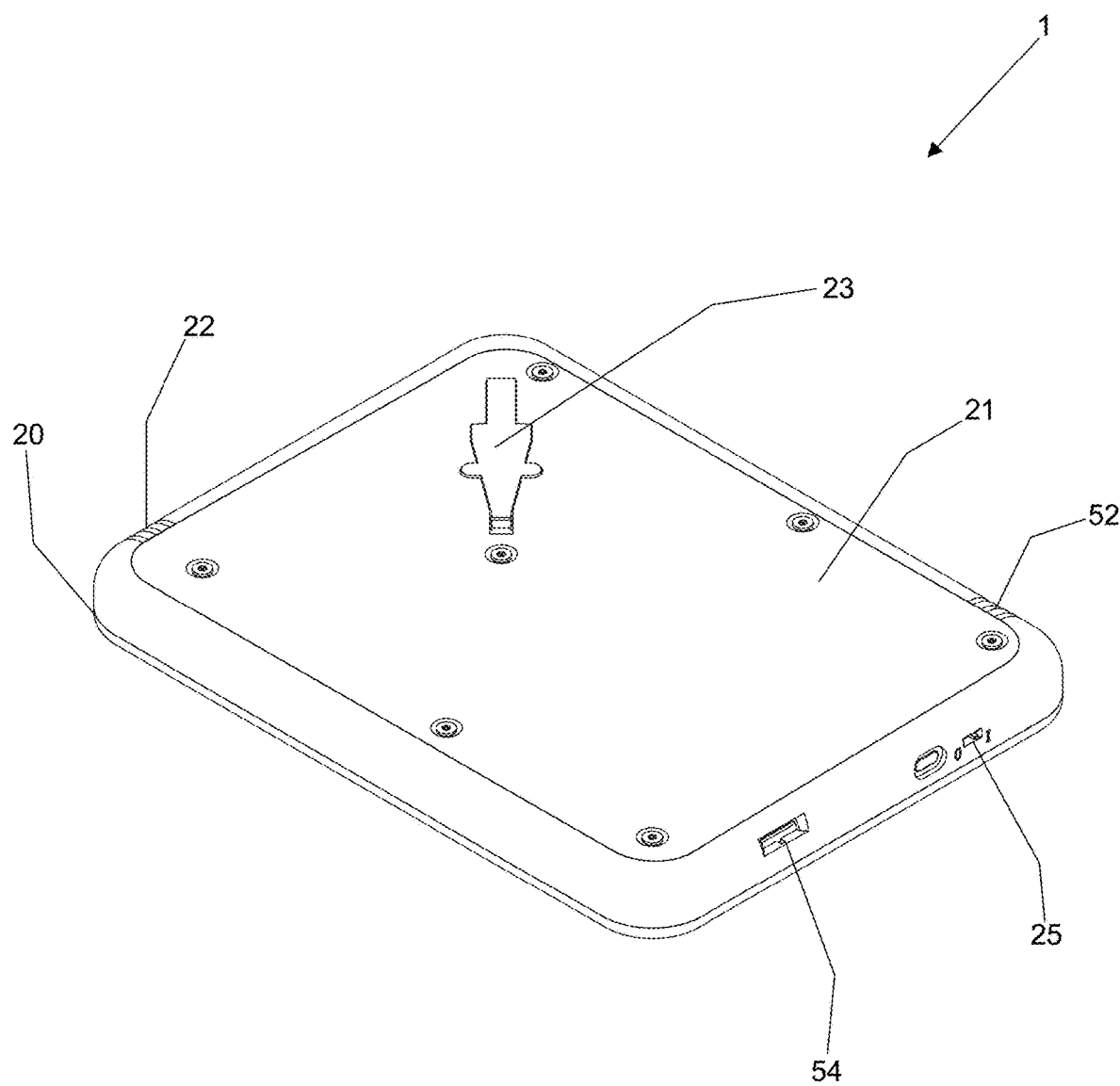
FIG. 2: Reverse perspective view of the wireless electromechanical device for demonstrating multiple fragrances or aromas.
Figure 3:
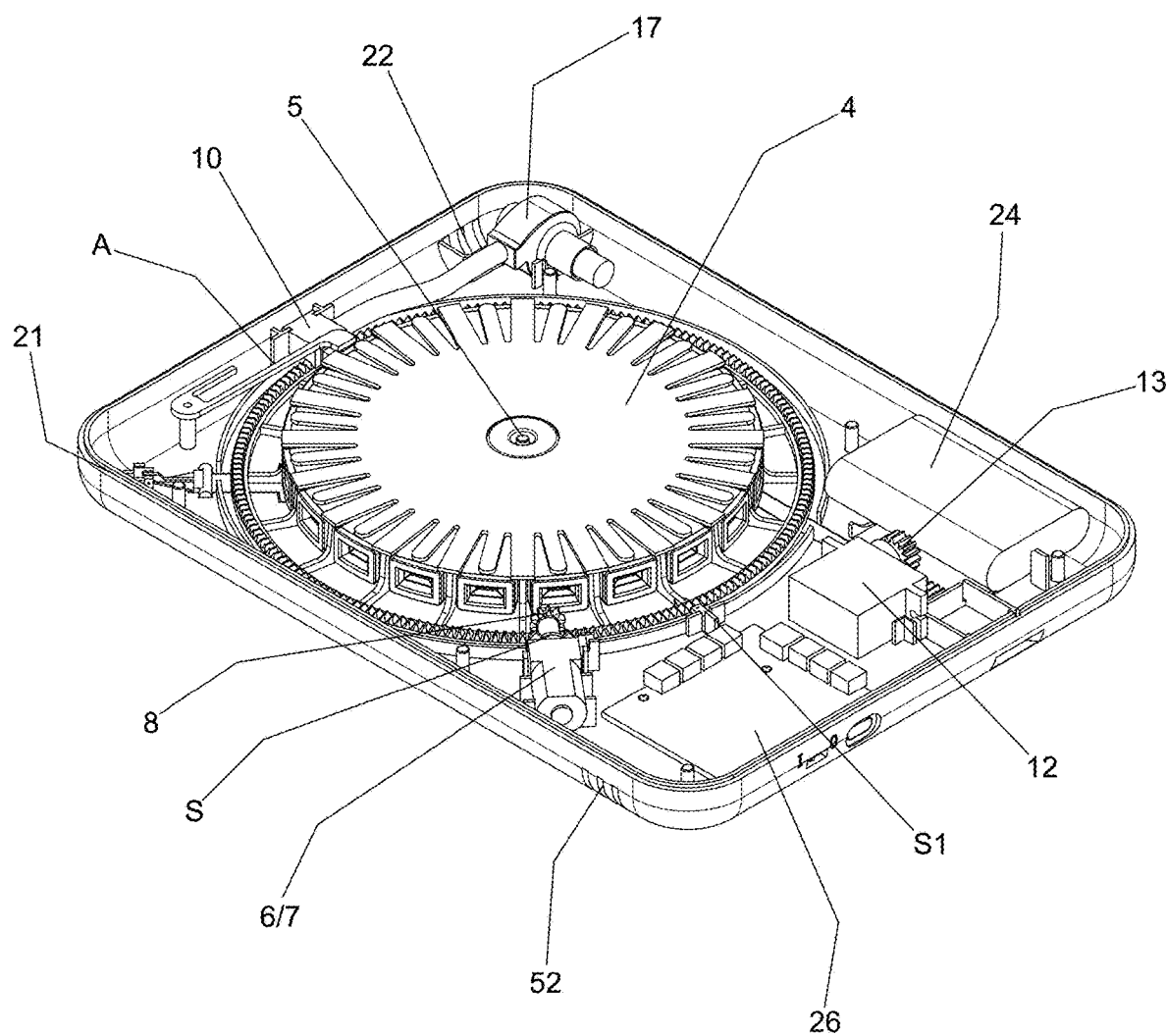
FIG. 3: A perspective view of the wireless electromechanical device for demonstrating multiple fragrances or aromas, without the top.
Figure 4:
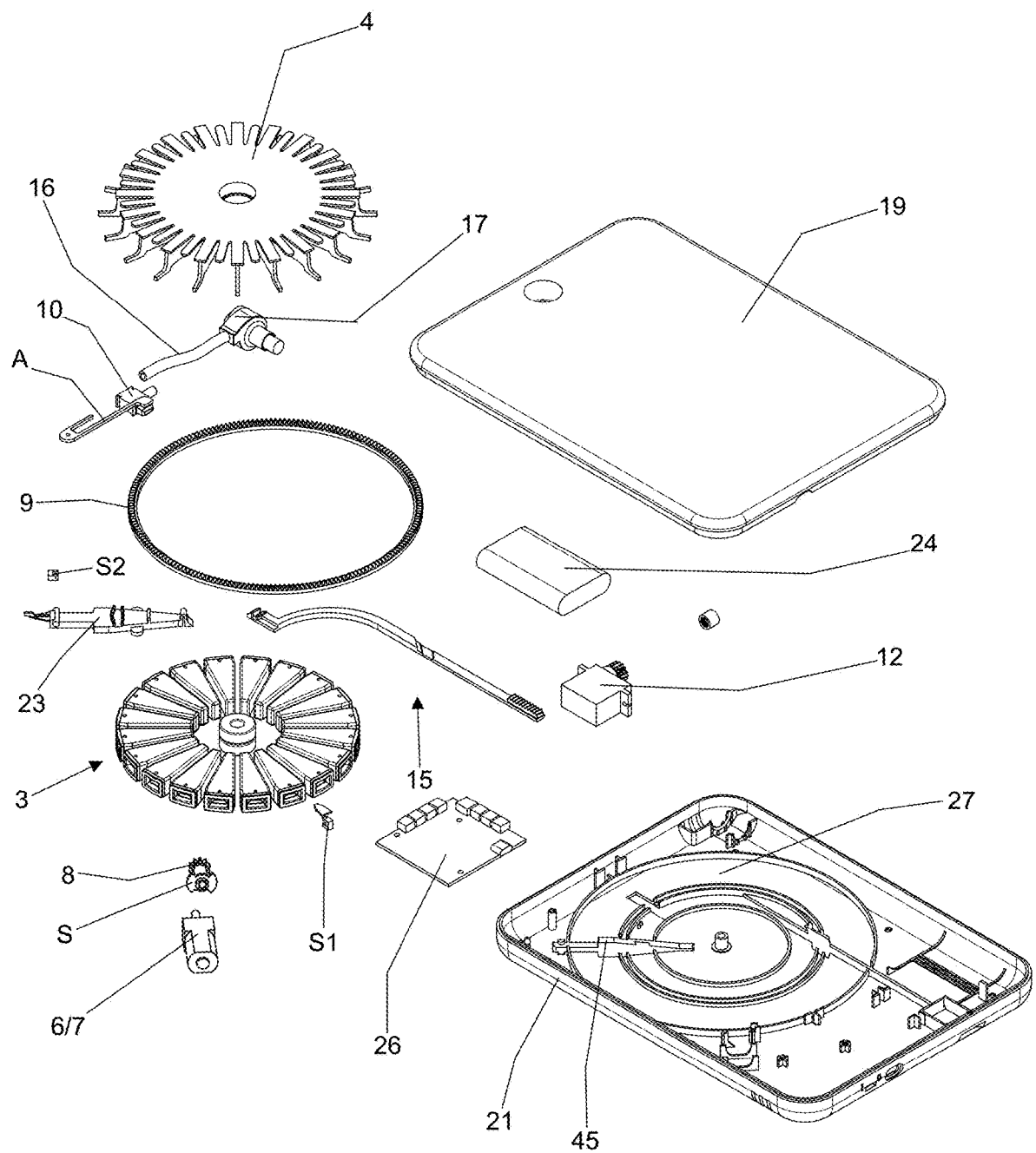
FIG. 4: An exploded perspective view of the wireless electromechanical device for demonstrating multiple fragrances or aromas.
Figure 5:
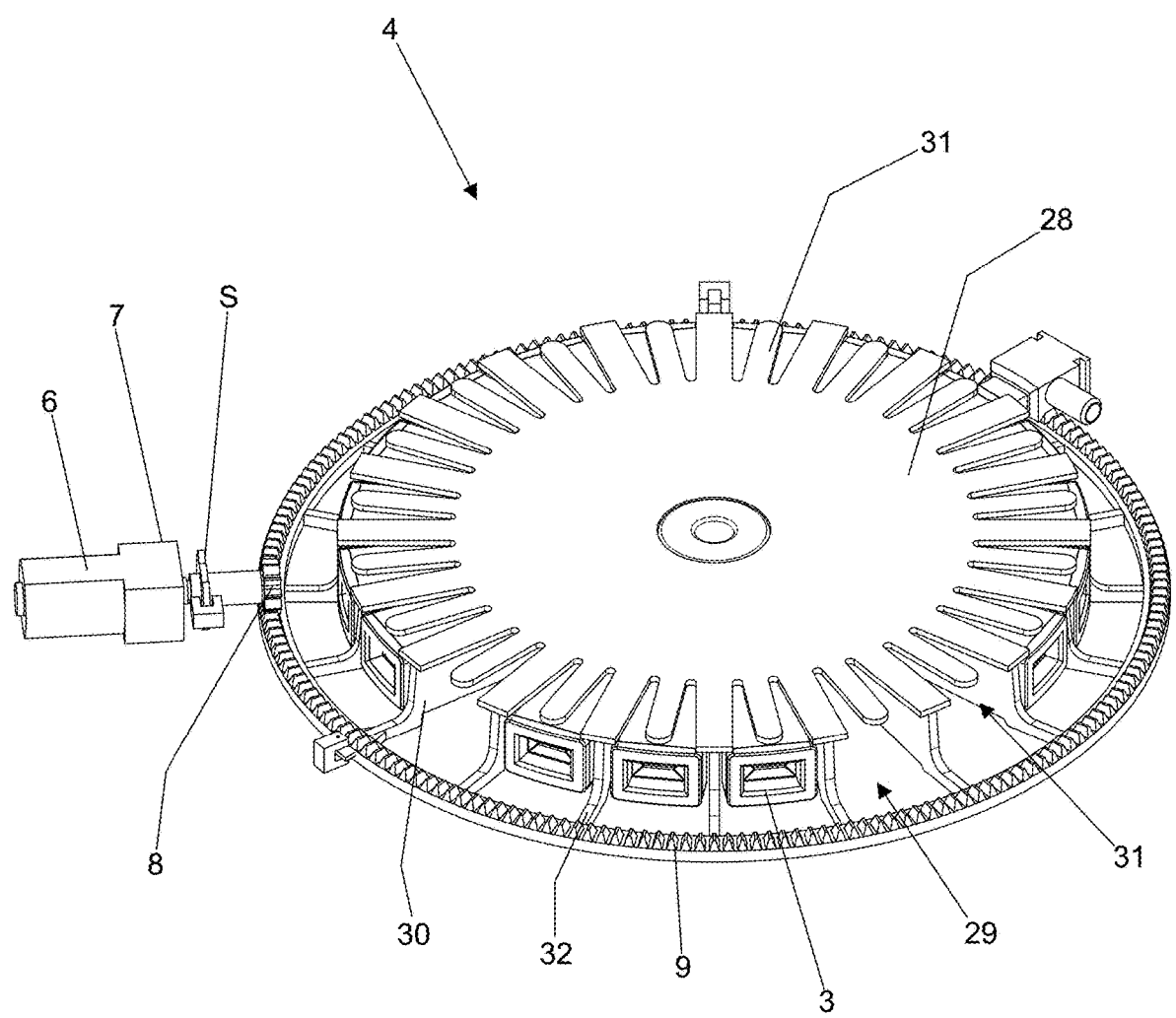
FIG. 5: A perspective view of the carousel and turning mechanism wireless electromechanical device for demonstrating multiple fragrances or aromas.
Figure 6:
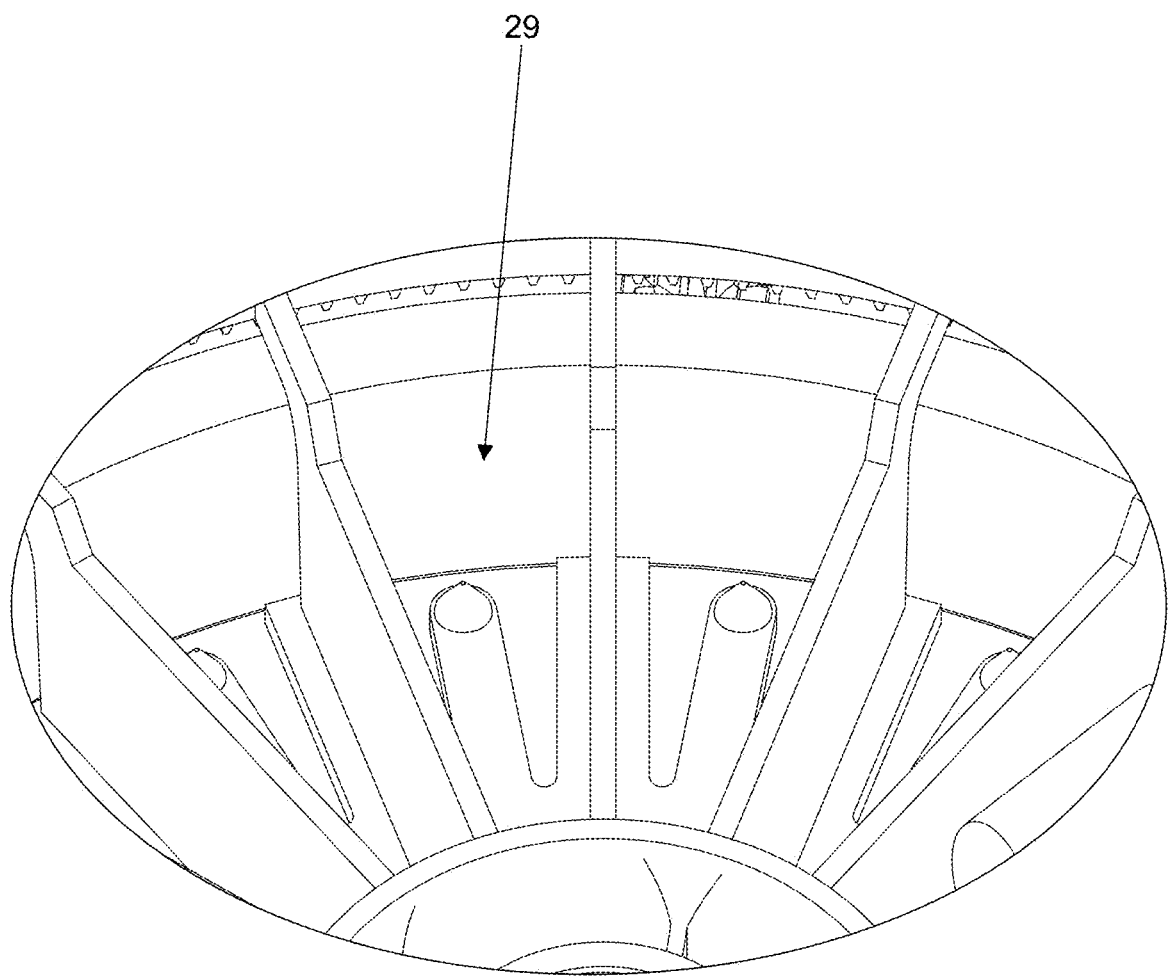
FIG. 6: Reverse perspective view of the carousel and turning mechanism wireless electromechanical device for demonstrating multiple fragrances or aromas.
Figure 7:
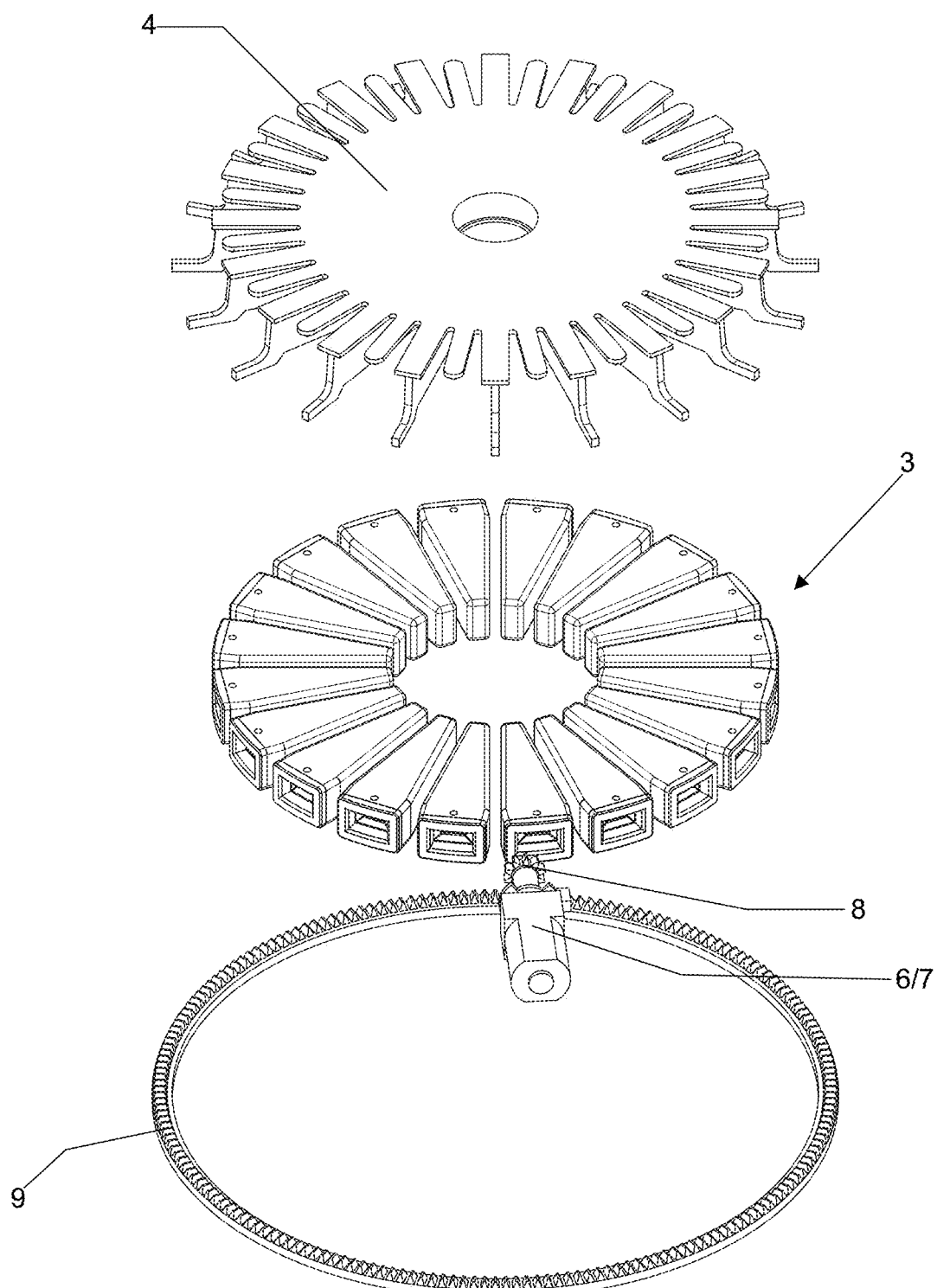
FIG. 7: An exploded perspective view of the set of the carousel and turning mechanism wireless electromechanical device for demonstrating multiple fragrances or aromas.
Figure 8:
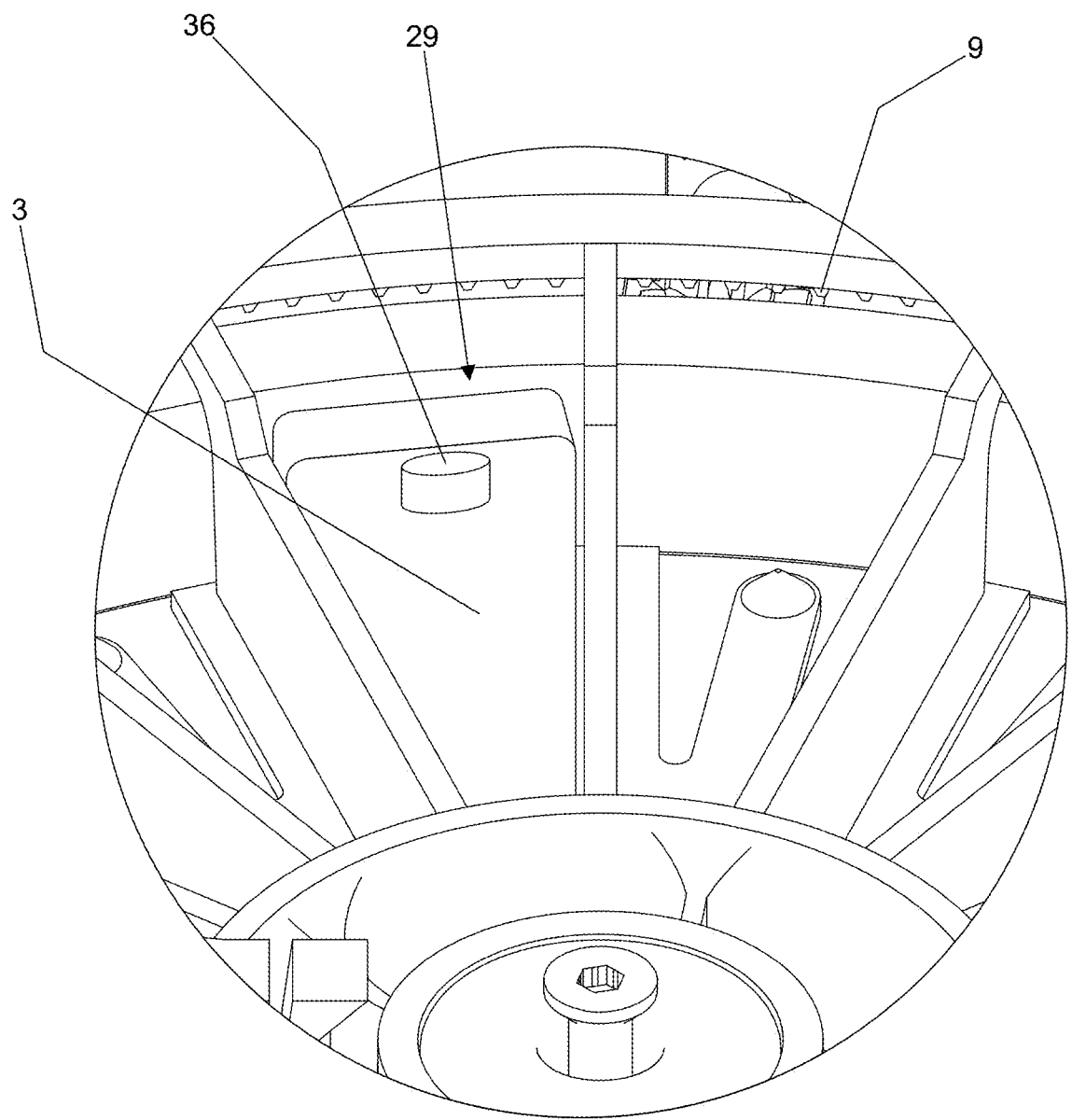
FIG. 8: A perspective view of the wireless electromechanical device for demonstrating multiple fragrances or aromas, showing the cartridge mounted on the carousel.
Figure 9:
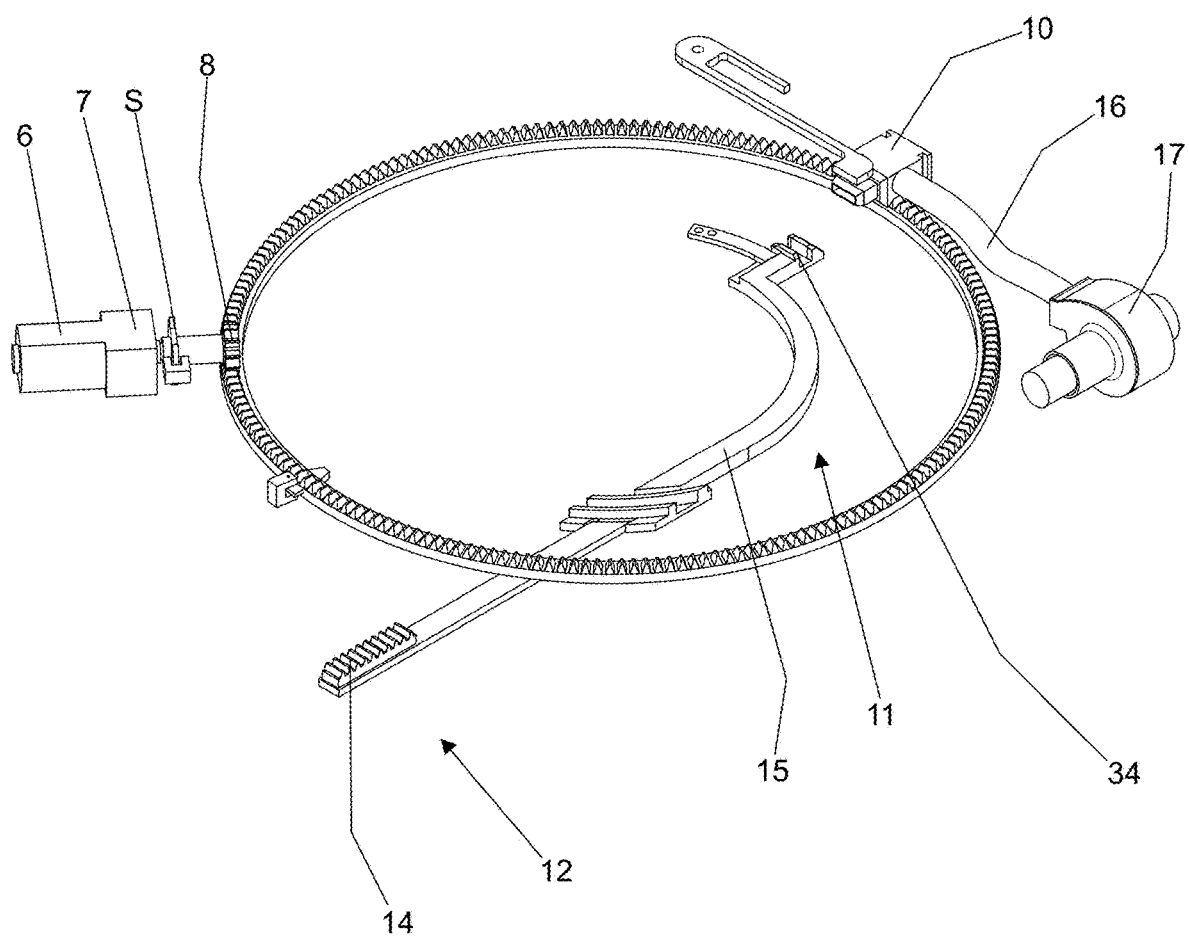
FIG. 9: A perspective view of the drive mechanism of the cartridge of the wireless electromechanical device for demonstrating multiple fragrances or aromas, shown without the carousel.
Figure 10:
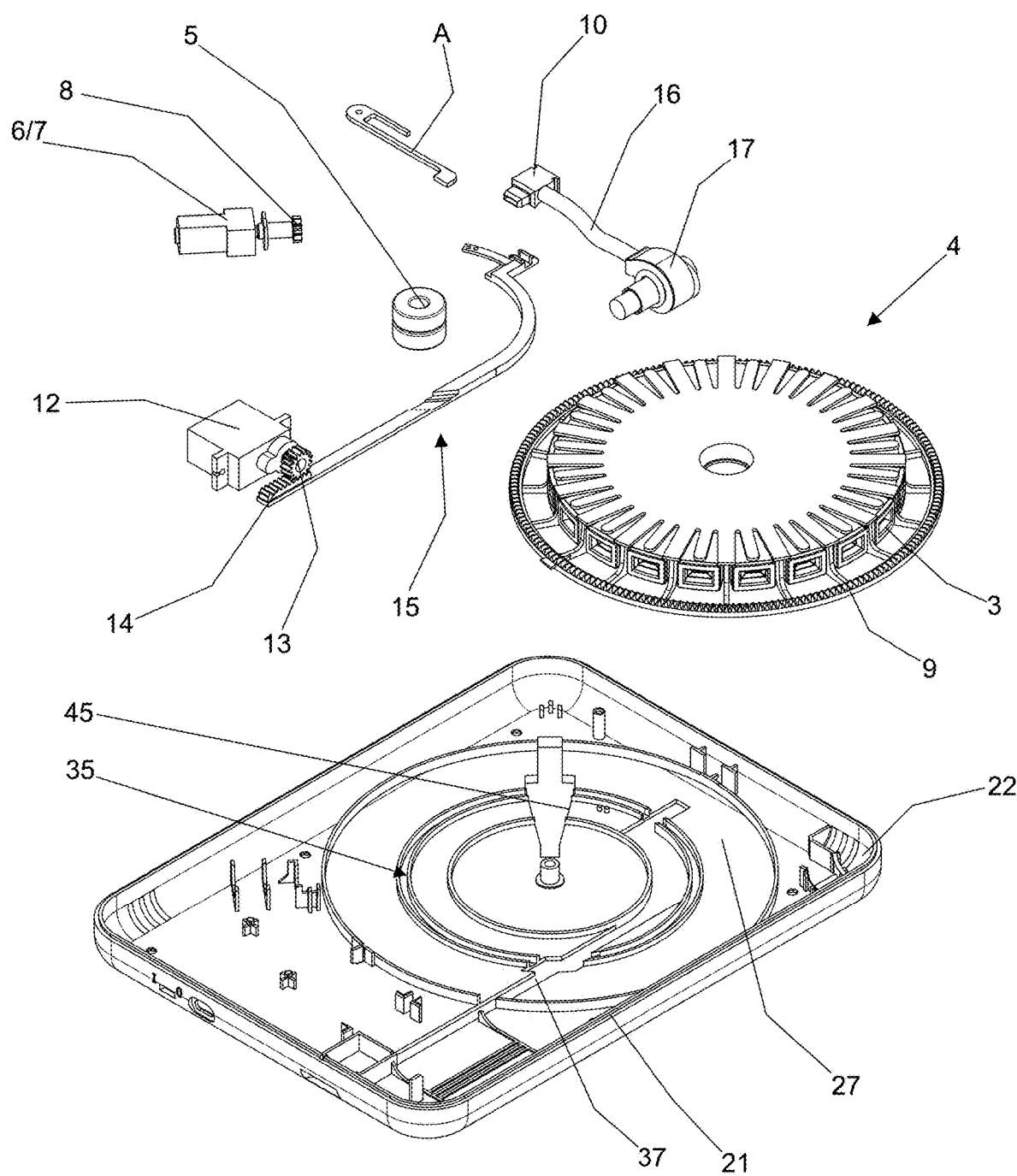
FIG. 10: An exploded perspective view of the forward mechanism of the cartridge of the wireless electromechanical device for demonstrating multiple fragrances or aromas, shown with the carousel and ventilation system.
Figure 11:
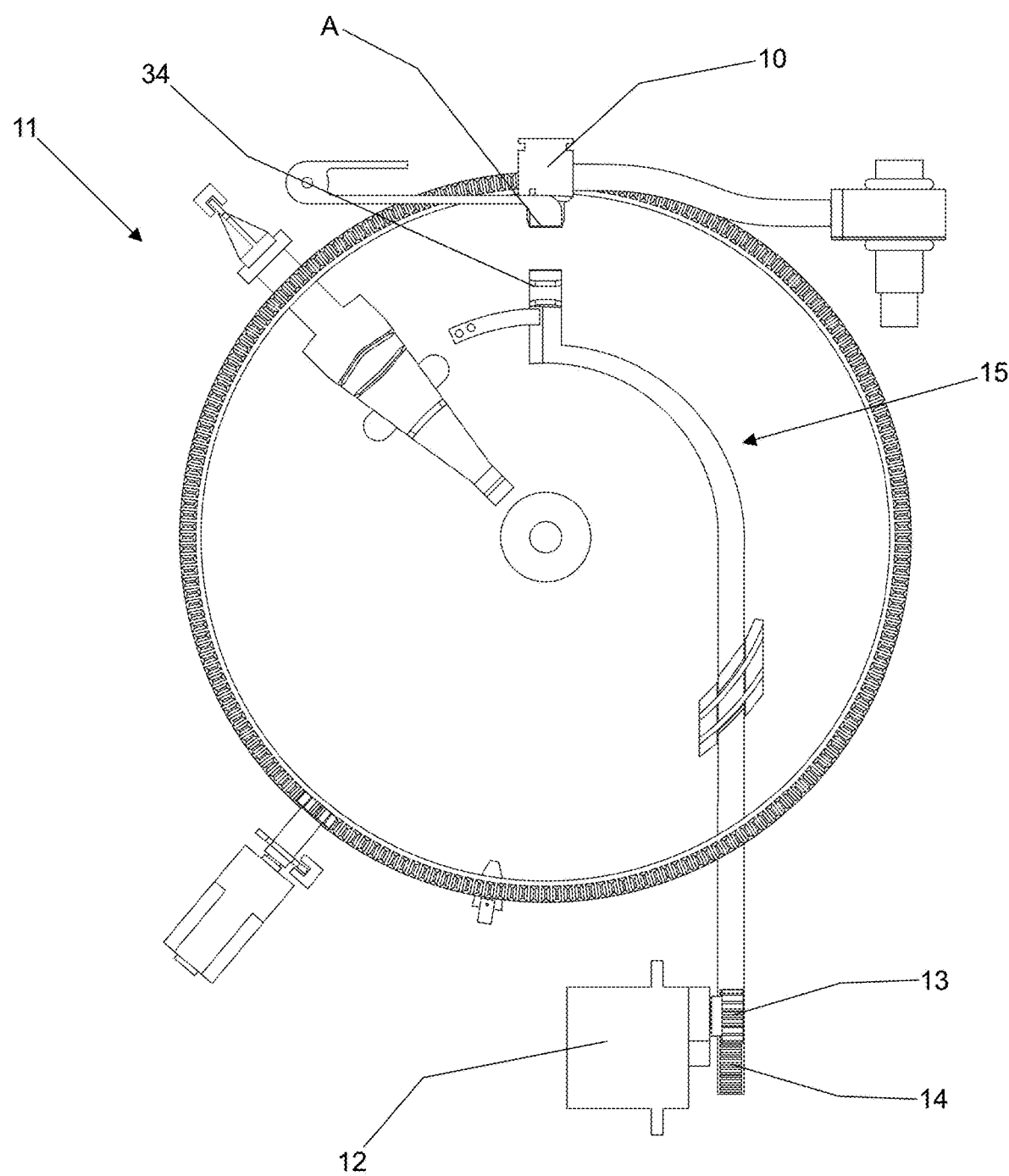
FIG. 11: A top view of the forward mechanism of the cartridge of the wireless electromechanical device for demonstrating multiple fragrances or aromas.
Figure 12:
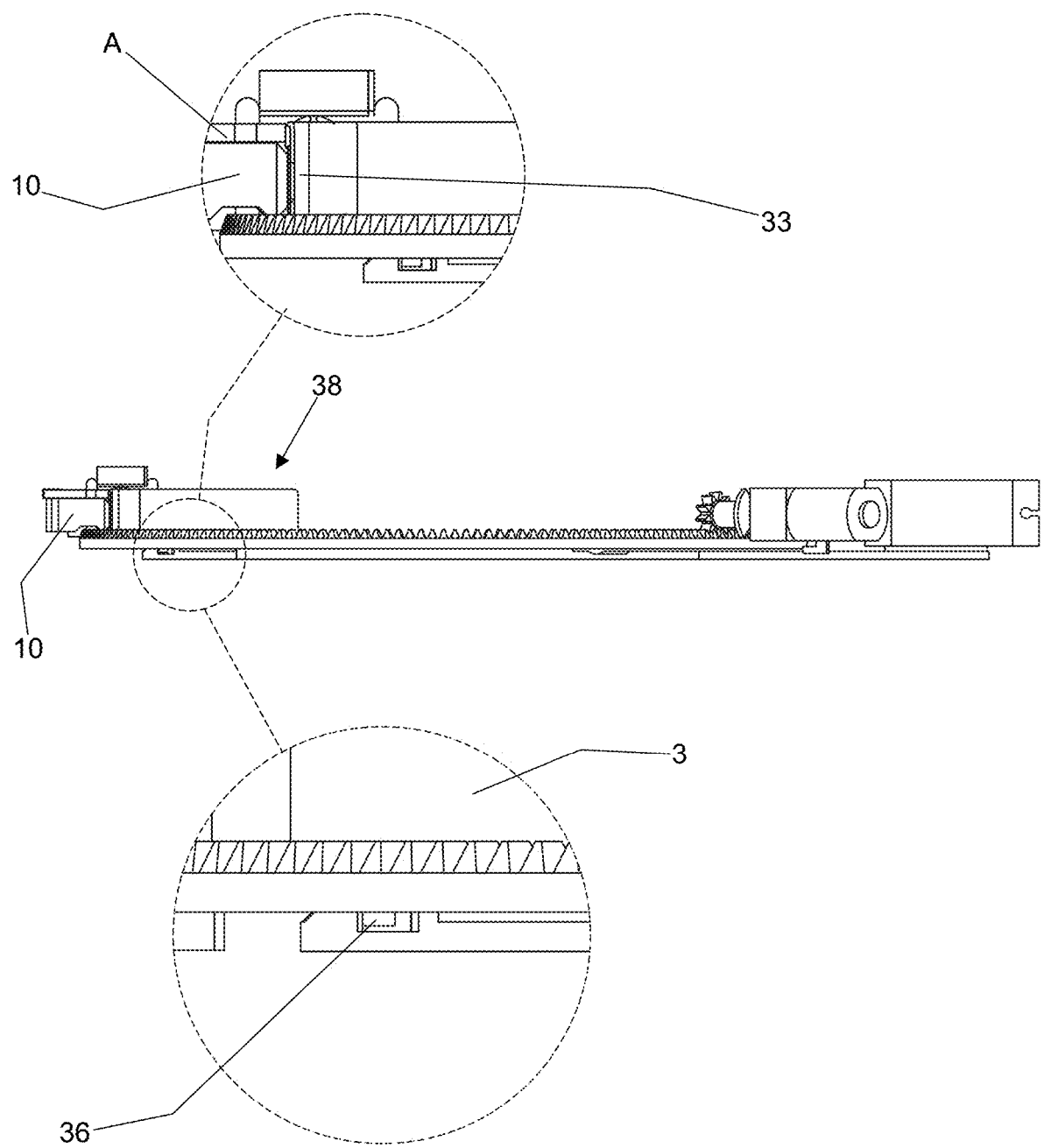
FIG. 12: A side view of the forward mechanism of the cartridge of the wireless electromechanical device for demonstrating multiple fragrances or aromas, with the cartridge recoiled and detail of the lower setting of the cartridge to the arm.
Figure 13:
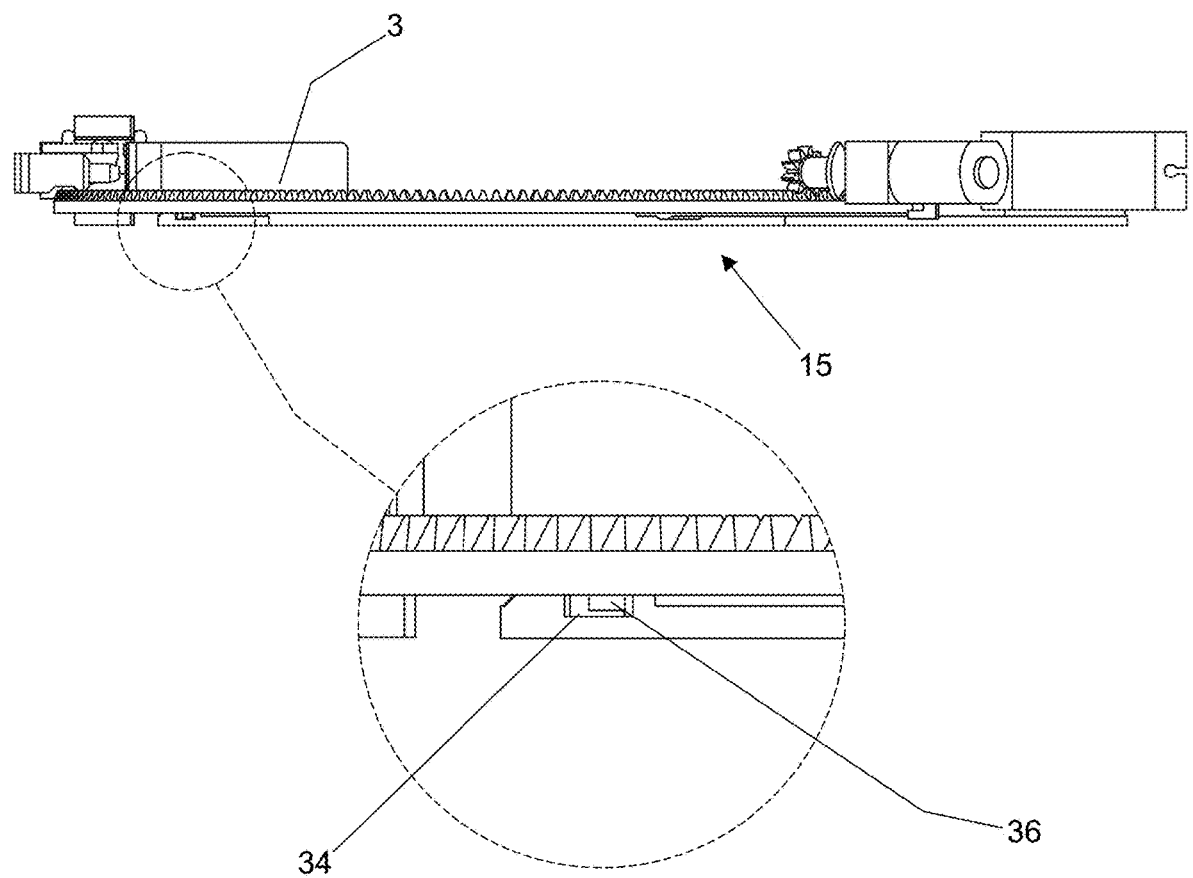
FIG. 13: A side view of the forward mechanism of the cartridge of the wireless electromechanical device for demonstrating multiple fragrances or aromas, with the cartridge advanced.
Figure 14:
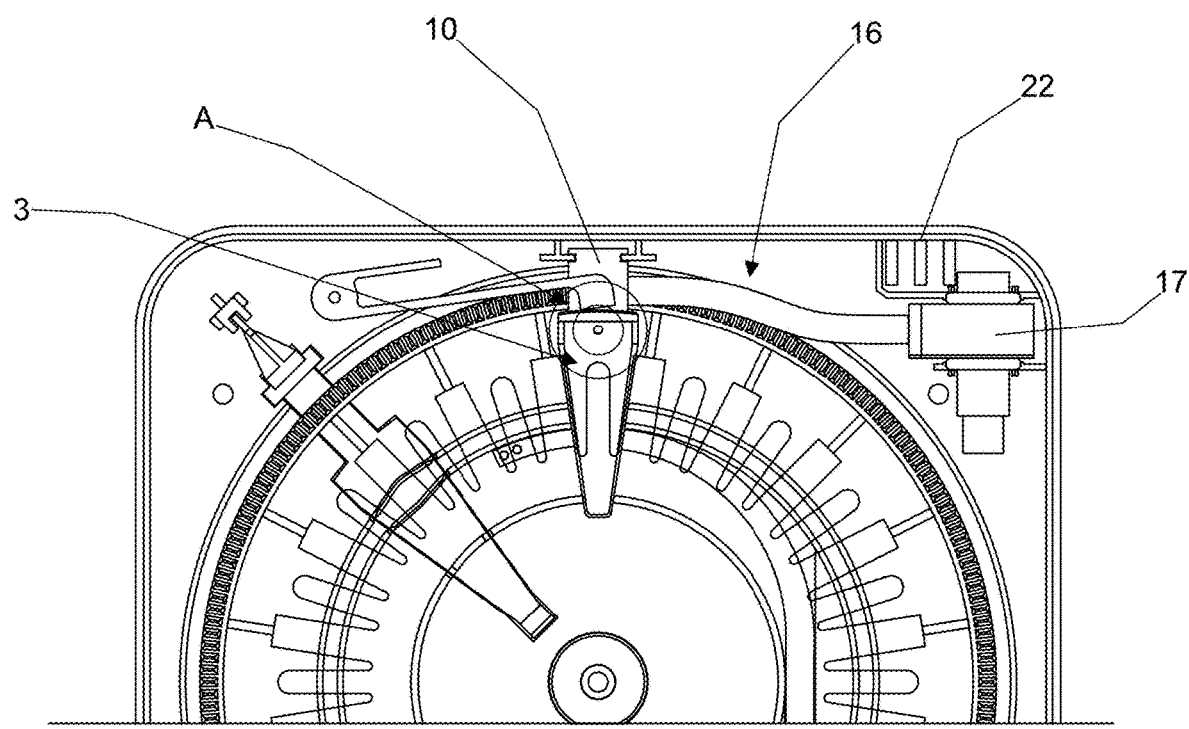
FIG. 14: A perspective view of the flexible ventilation hose of the cartridge of the wireless electromechanical device for demonstrating multiple fragrances or aromas, with detail of the air intake orifice.
Figure 15:
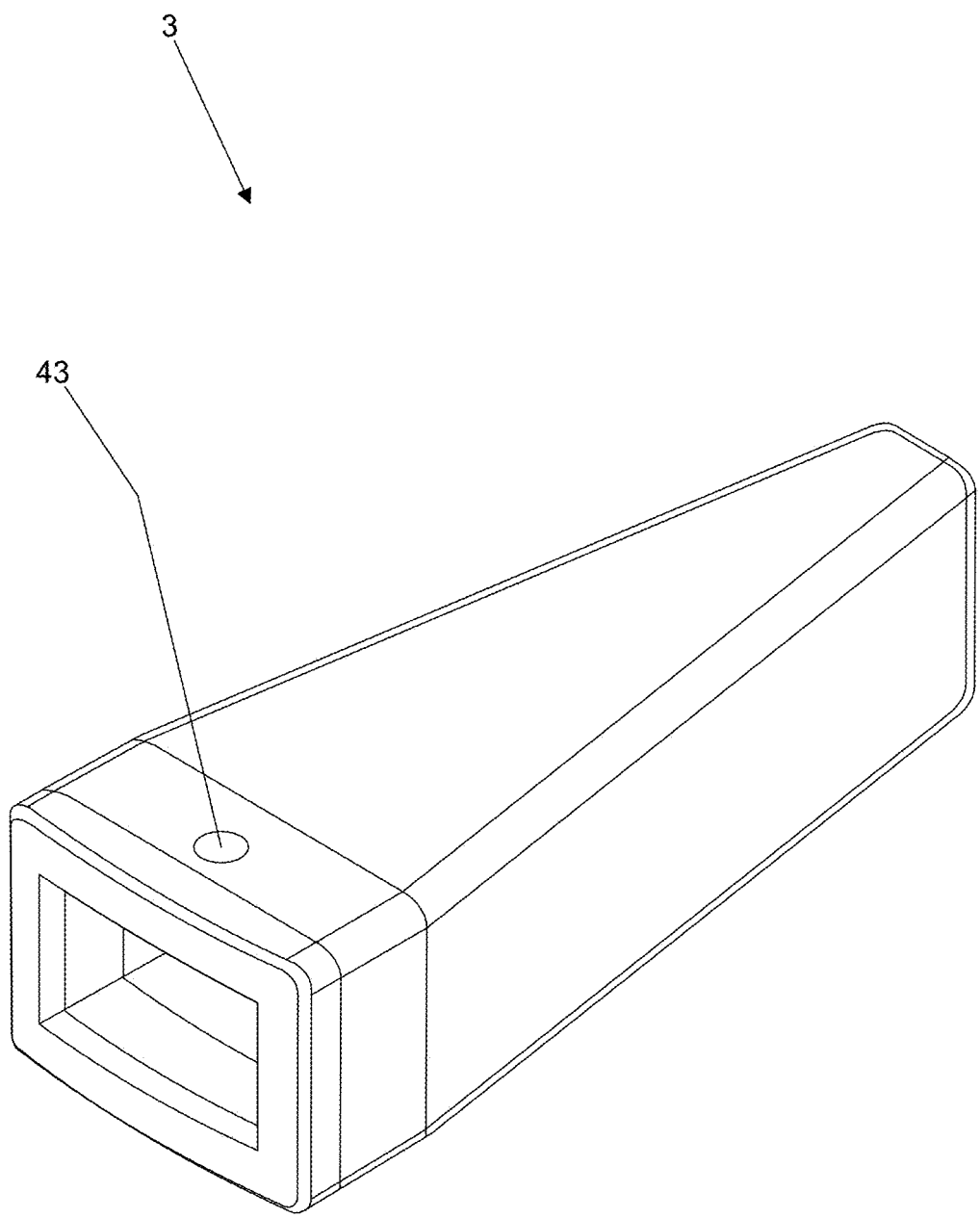
FIG. 15: A perspective view of the cartridge of the forward mechanism of the cartridge of the wireless electromechanical device for demonstrating multiple fragrances or aromas.
Figure 16:
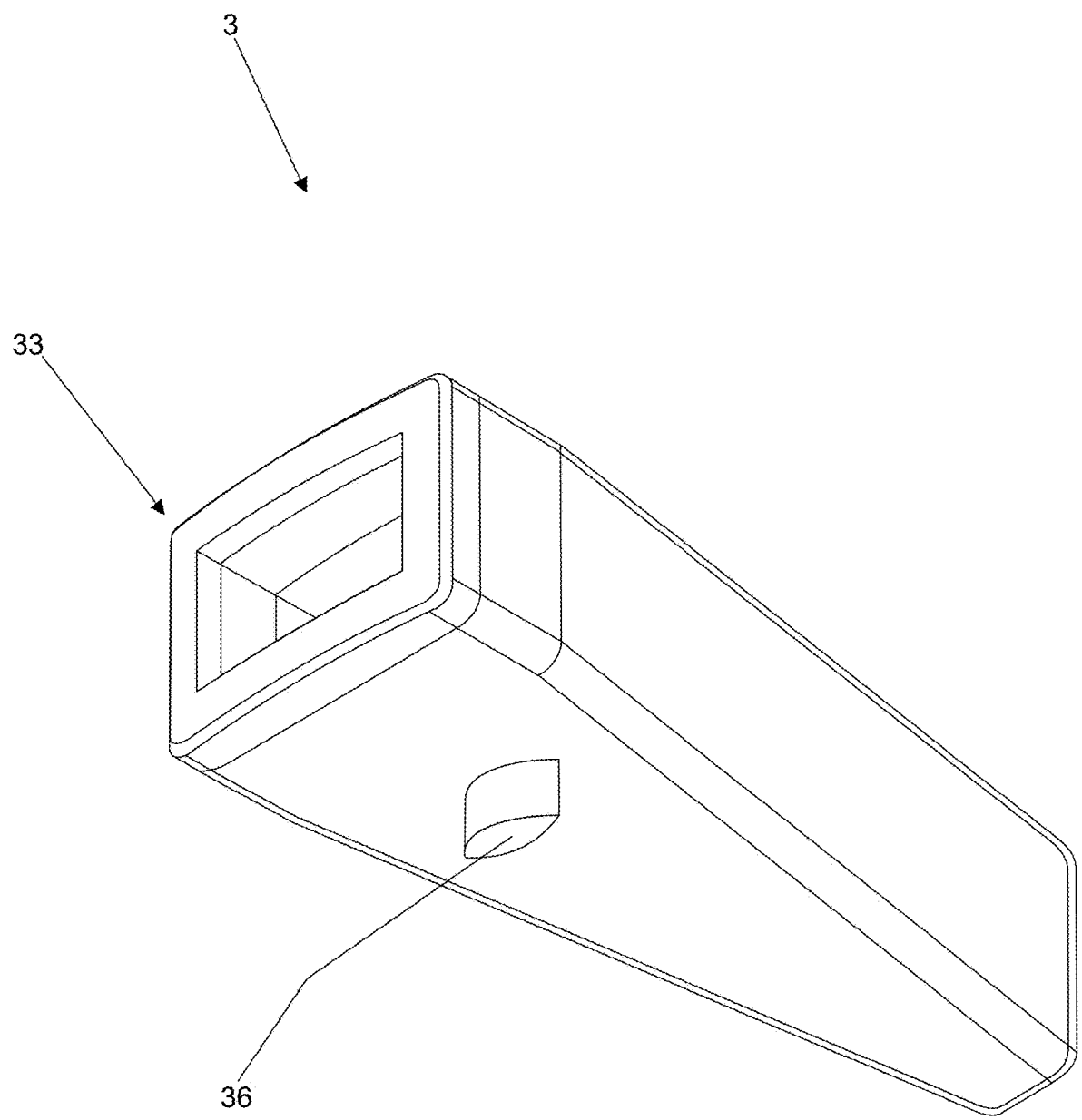
FIG. 16: Reverse perspective view of the cartridge of the forward mechanism of the cartridge of the wireless electromechanical device for demonstrating multiple fragrances or aromas.
Figure 17:
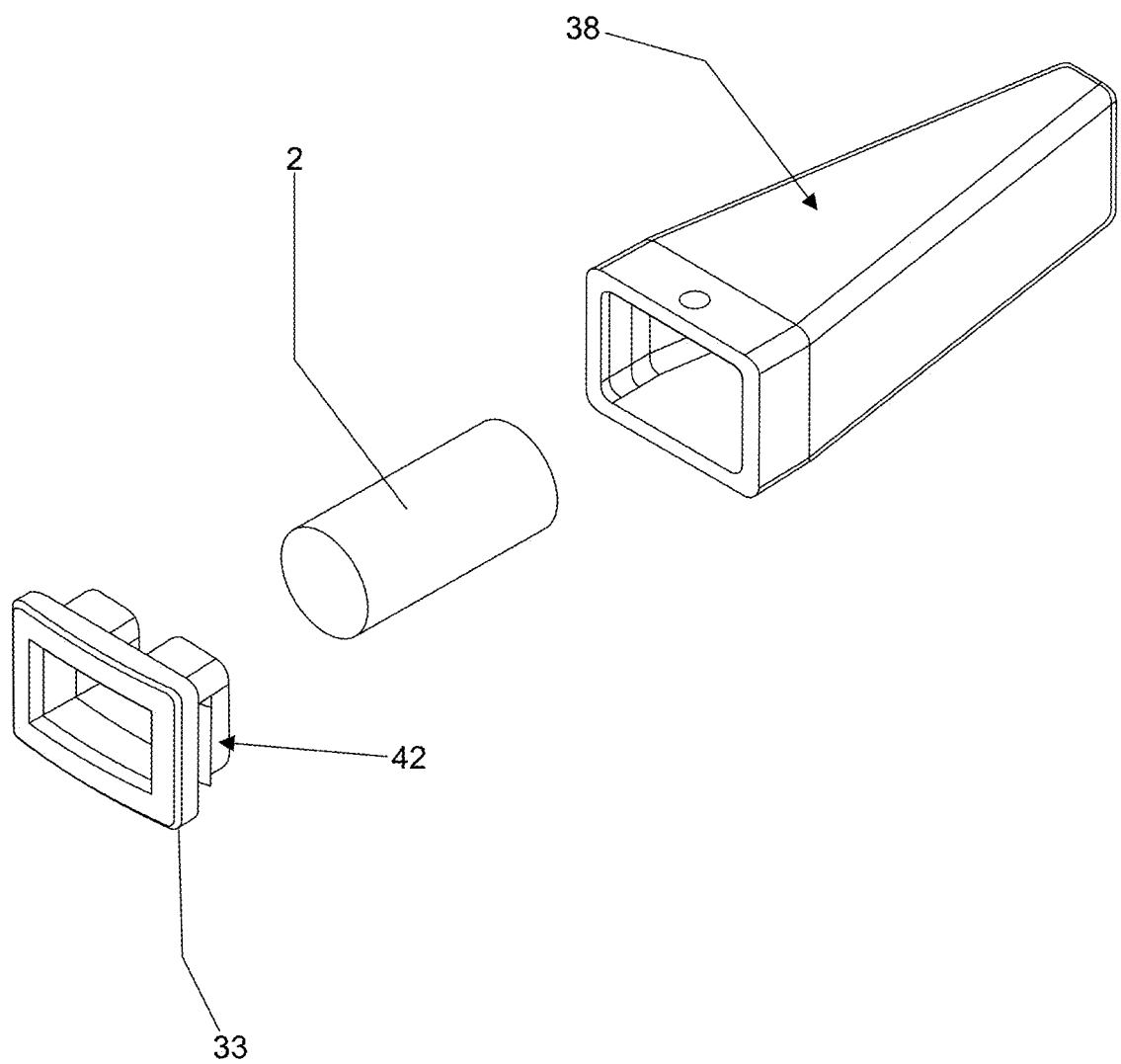
FIG. 17: An exploded perspective view of the cartridge of the wireless electromechanical device for demonstrating multiple fragrances or aromas, shown the air flow.
Figure 18:
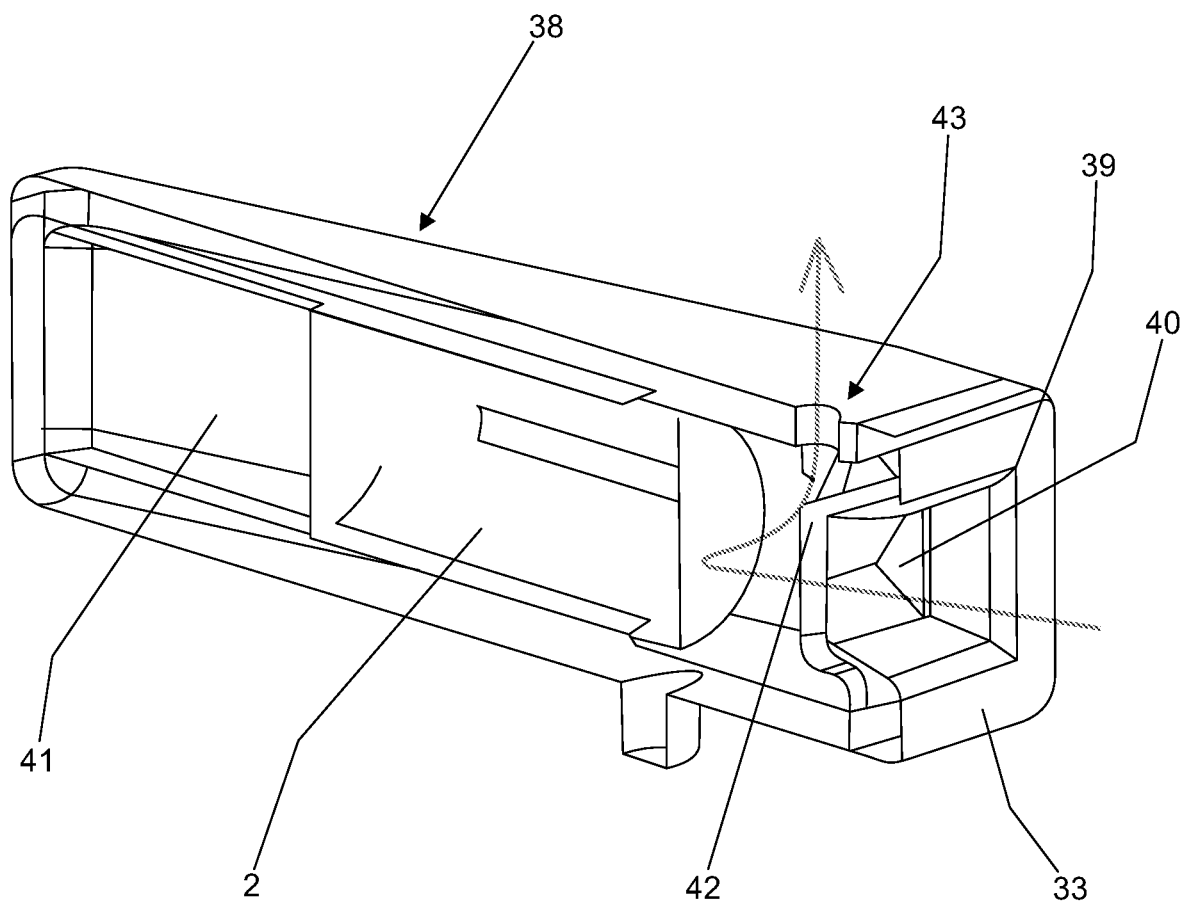
FIG. 18: A cutaway view of the cartridge of the wireless electromechanical device for demonstrating multiple fragrances or aromas, shown the air flow, with detail inferior of the passage of air of the header.
Figure 19:
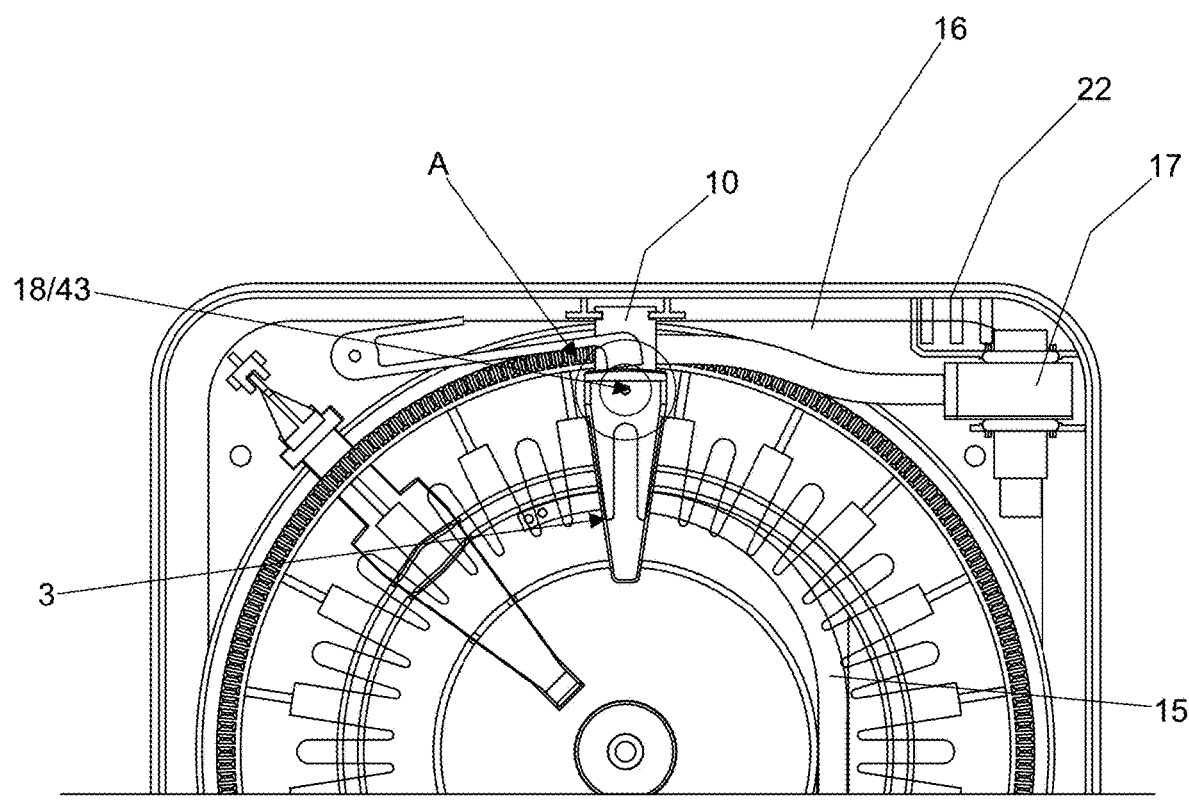
FIG. 19: Upper schematic view illustrating the cartridge of the wireless electromechanical device for demonstrating multiple fragrances or aromas, in a forward position to release the fragrance.
Figure 20:
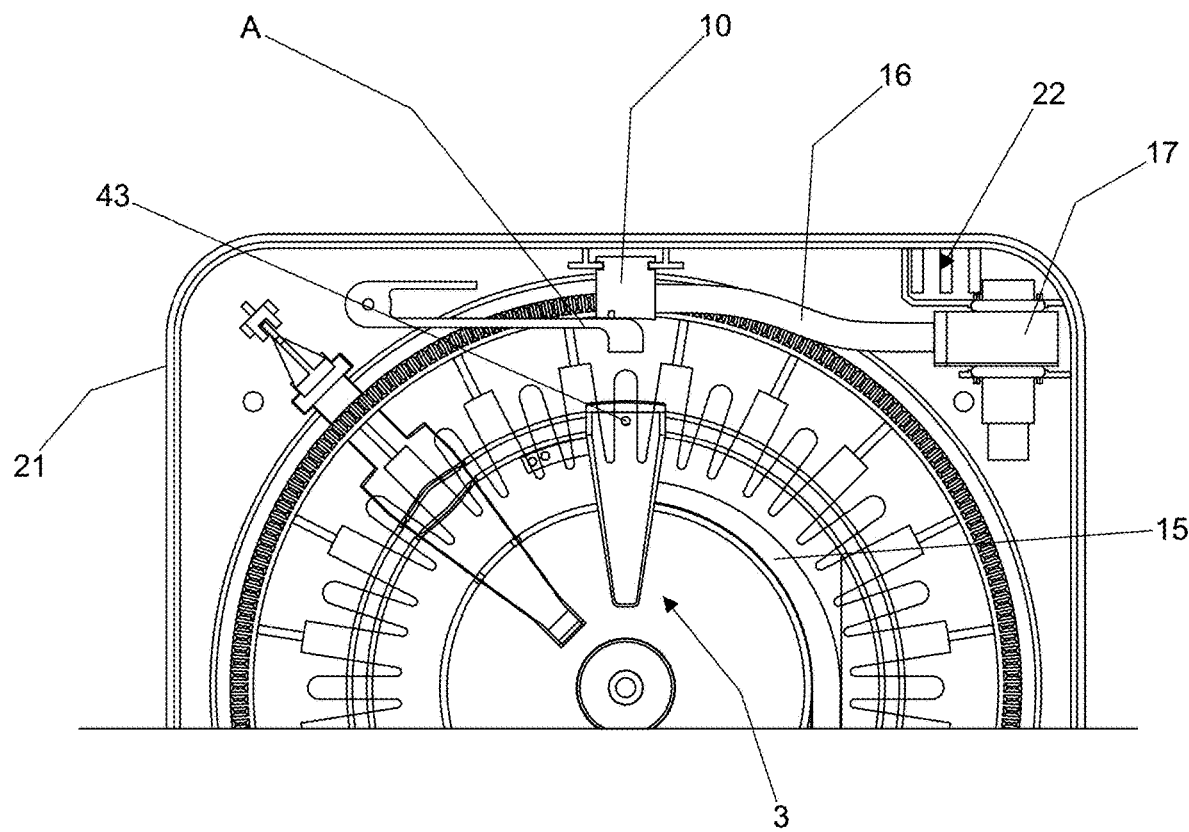
FIG. 20: Upper schematic view illustrating the cartridge of the wireless electromechanical device for demonstrating multiple fragrances or aromas, in a recoiled position to retain the fragrance.
Figure 21:
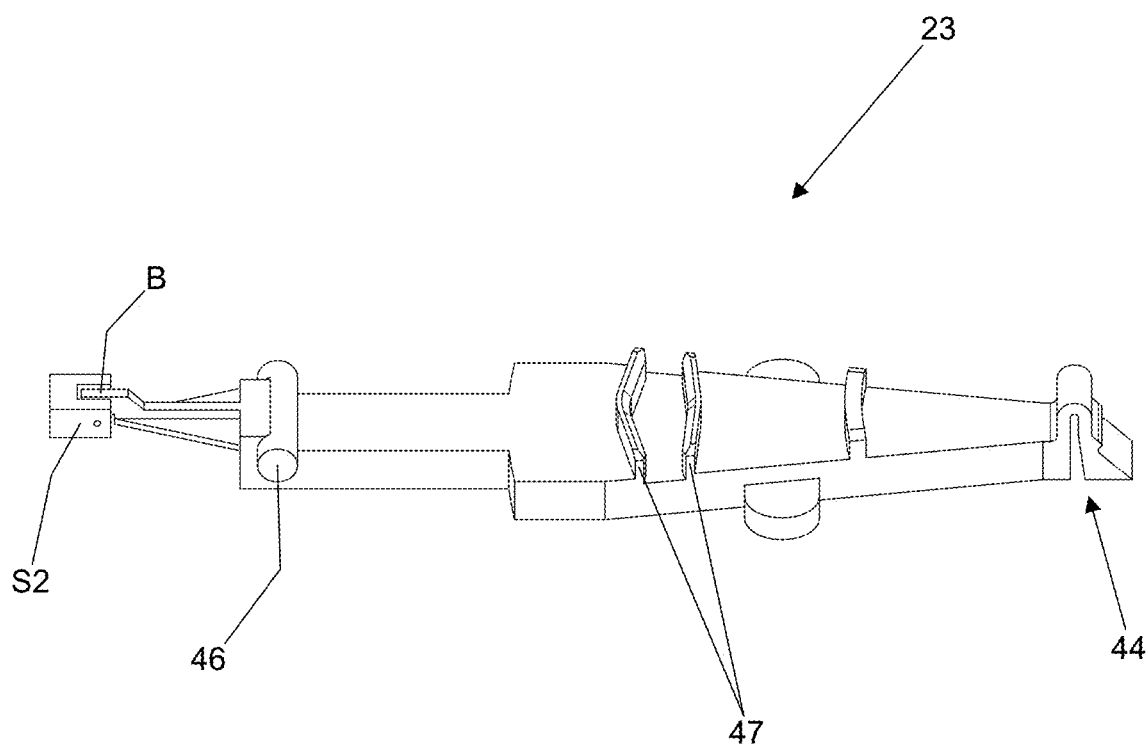
FIG. 21: A perspective view of the wireless electromechanical device for demonstrating multiple fragrances or aromas, showing the top for changing the cartridge.
Figure 22:
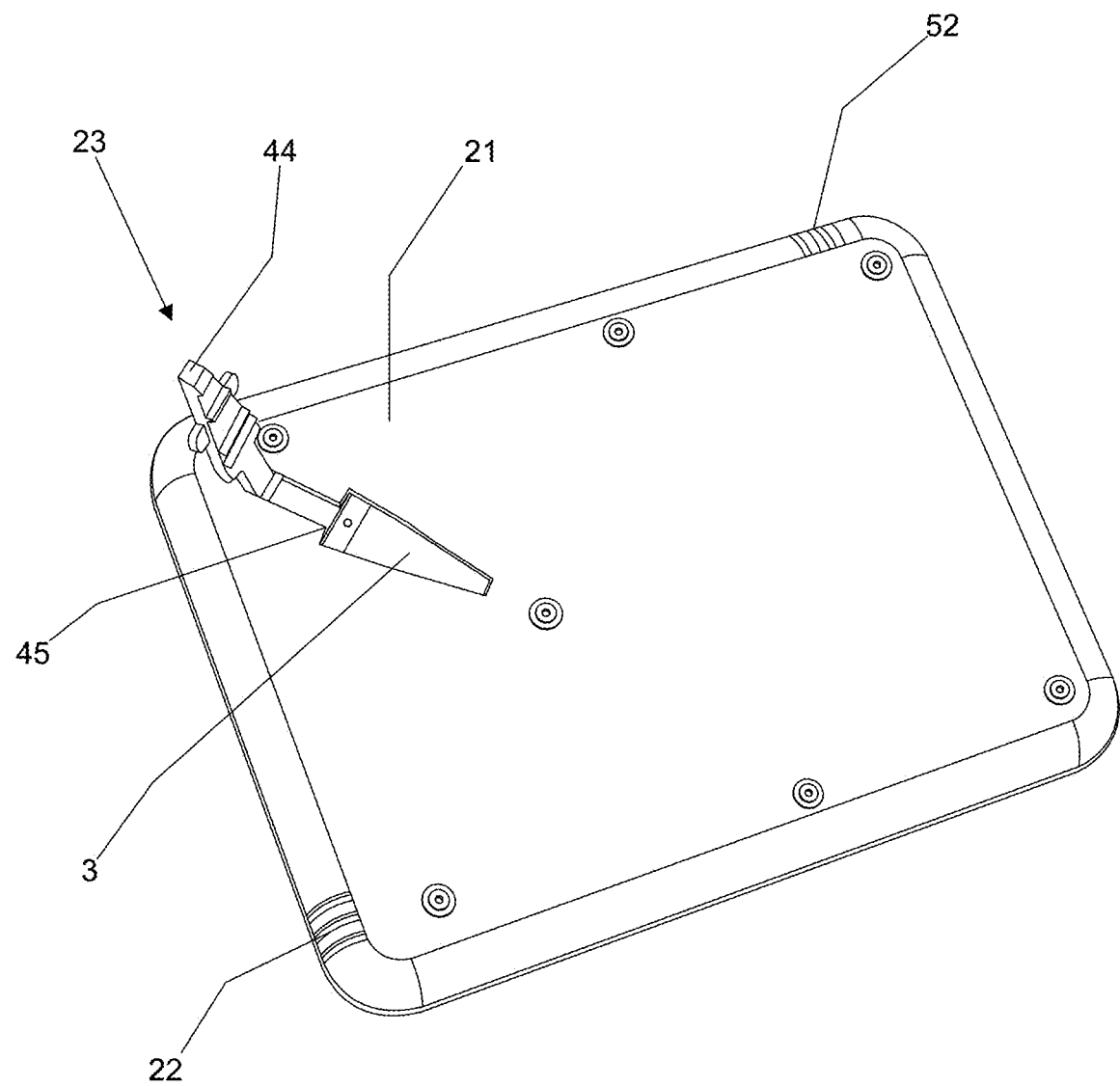
FIG. 22: A perspective view of the wireless electromechanical device for demonstrating multiple fragrances or aromas, showing the top for changing the cartridge installed and in open position.
Figure 23:
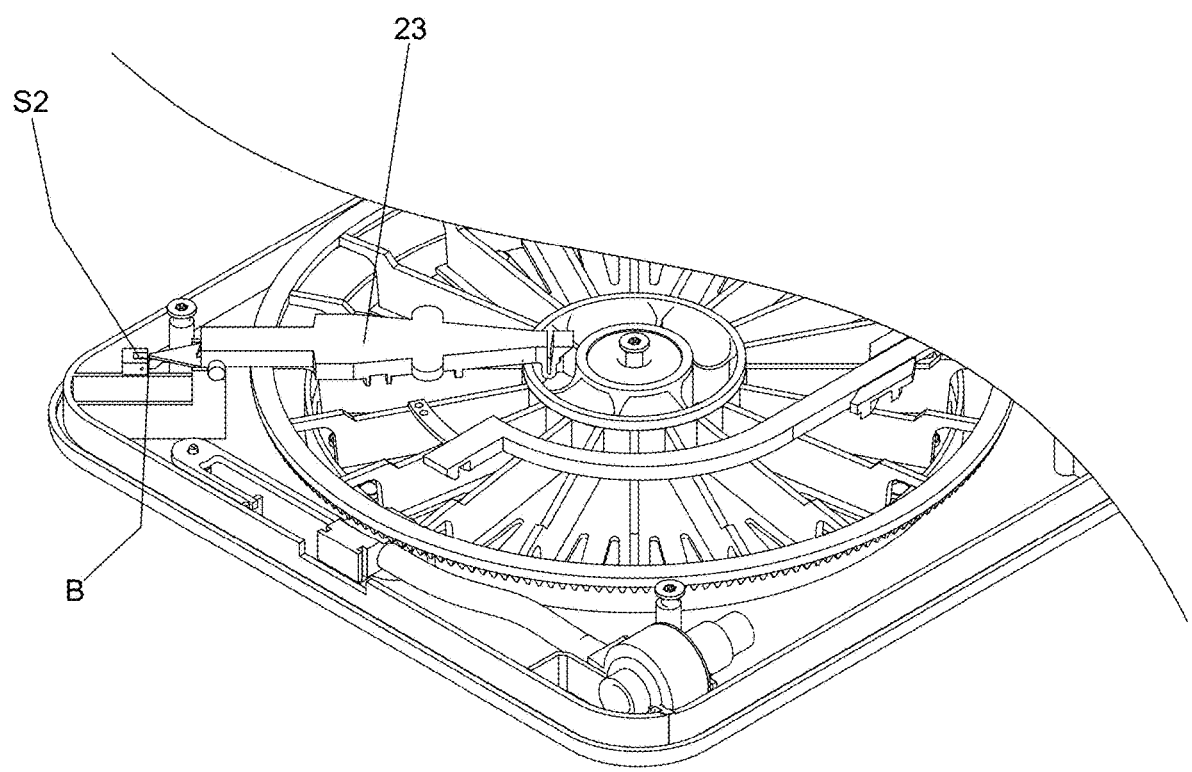
FIG. 23: A perspective view of the wireless electromechanical device for demonstrating multiple fragrances or aromas, showing the top sensor for changing the open cartridge.
Figure 24:
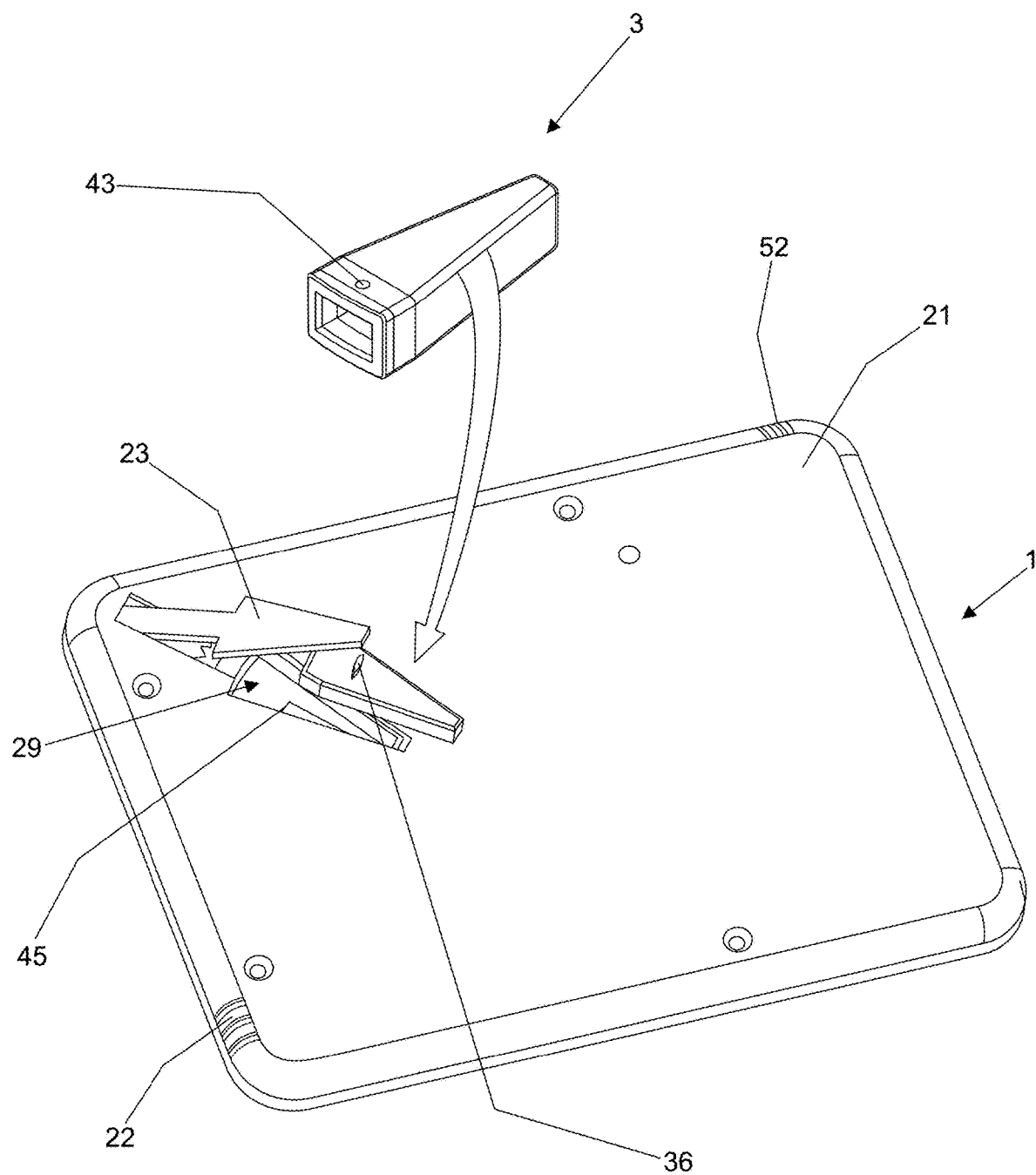
FIG. 24: A perspective view of the wireless electromechanical device for demonstrating multiple fragrances or aromas, showing the change of the cartridge.
Figure 25:
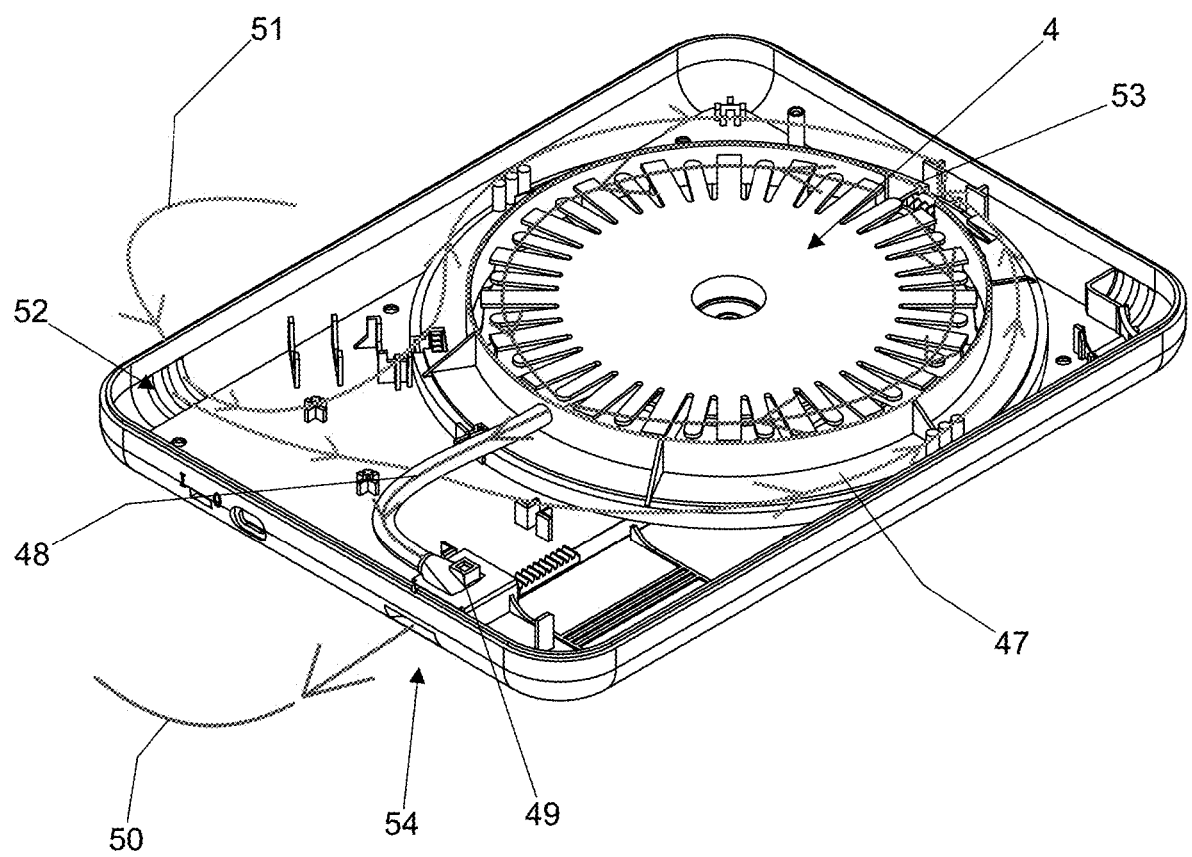
FIG. 25: A schematic perspective view of the wireless electromechanical device for demonstrating multiple fragrances or aromas, showing optional autoclean mechanism.
Figure 26:
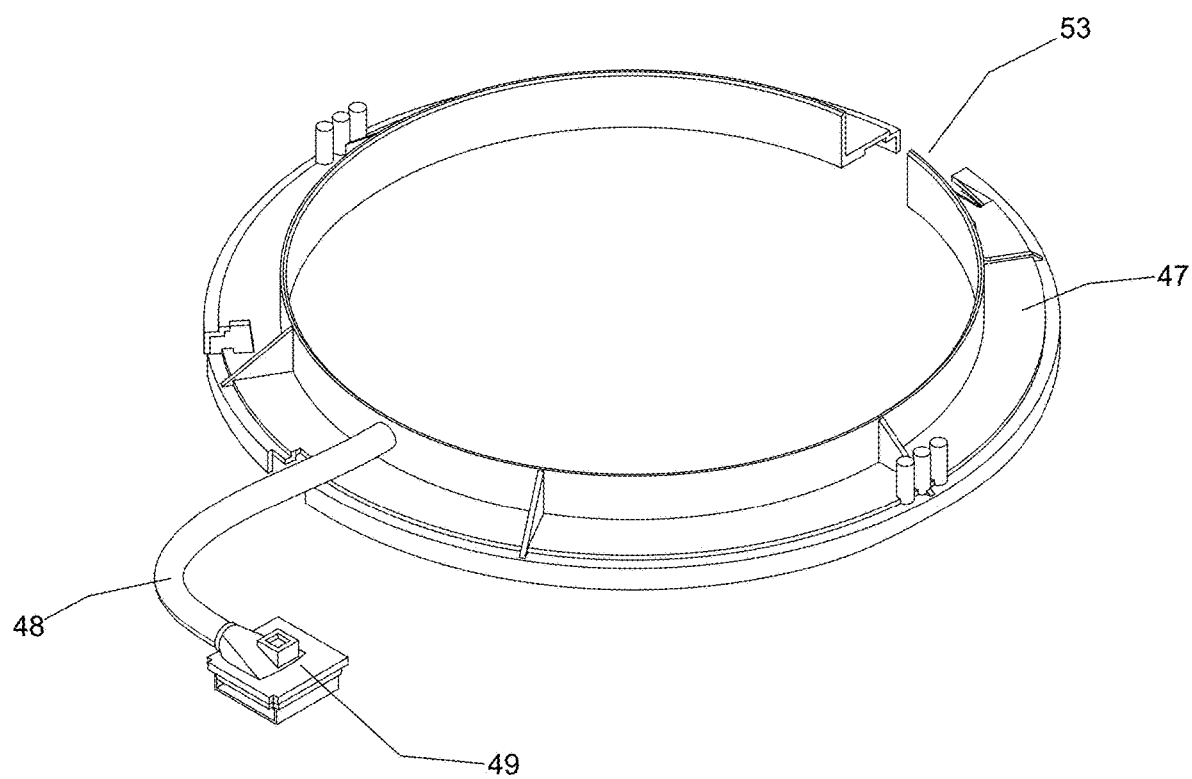
FIG. 26: A perspective view of the wireless electromechanical device for demonstrating multiple fragrances or aromas, showing optional autoclean mechanism components.

The "WIRELESS ELECTROMECHANICAL DEVICE FOR DEMONSTRATING MULTIPLE FRAGRANCES OR AROMAS", includes an electromechanical device (1), which acts like an electronic catalog for the olfactory testing of different fragrances or aromas, contained in an absorbent cylindrical element (2) inserted into individual cartridges (3), which are interchangeable and encased in a carousel (4), supported on central bearings (5) and radially moved by means of an electric motor (6) with reducer (7) and gearing (8) which acts on a circular rack (9). Upon receipt of a command, via application, the carousel (4) turns, positioning the cartridge (3), corresponding to the fragrance or aroma chosen, in front of the connector nozzle (10), thanks to a positioning sensor (S), which counts the turns of the shaft of the electric motor (6). Next, a mechanical actuator (11) formed by electric motor (12), gearing (13) which operates on a straight rack (14), which in turn drives a drawing cane (15), which pushes, and then retracts the cartridge, (3) inside the connector nozzle (10), and jointly with the air flow coming from a flexible hose (16), from where the air inflated by a compressor (17) enters said cartridge (3), forces the emission of the scent through the outlet orifice (18) of the top (19) of the box (20), thus providing the user a reliable olfactory testing.

More particularly, electromechanical device (1) claimed is formed by a bipartite box (20), having a bottom (21) endowed with tears (22) at the side end, for air intake in the compressor (17) and port (23) for recharging the cartridges (3), and a top (19) with outlet orifice (18) of the fragrances. The bottom (21) contains a rechargeable battery (24), which is provided with energy by means of external connectors (25), with the objective of powering an electronic circuit (26) responsible for the interface application/electromechanical device (1) and for the correct location of the cartridge (3), performed by the sensor and positioning (S), containing a fragrance chosen by the user, in relation to the connector nozzle (10). Lastly, the box (20) also comprises an electric motor (6) for driving the turning mechanism of the carousel (4), which receives the cartridges (3), besides an electric motor (12) for driving the mechanical actuator (11), as well as the compressor (17) and an easy-to-assemble flexible hose (16) which receives the air coming from the compressor (17), leading it to the connector nozzle (10).

The electromechanical device (1), which, as already commented upon, is nothing more than an electronic catalog with different fragrances, contained in an absorbent cylindrical element (2) inserted into the individual cartridges (3), operates as follows.

As soon as the electromechanical device (1) is switched on, a calibration sensor (S1) places the reference cartridge (3) in line with the connector nozzle (10). Next, the cartridge (3), with the fragrance chosen by the user in the application, begins turning for alignment in the emission position, that is, in front of the connector nozzle (10), using the positioning sensor (S) installed in the shaft of the motor (6)/reducer (7) showing the number of turns of this shaft with the position of the cartridges (3). The carousel (4) is turned by means of an electric motor (6), reducer (7) in whose there is coupled a gearing (8) which acts on a circular rack (9) solidary to the carousel (4), which turns, as already commented upon, until the selected cartridge (3) aligns with the connector nozzle (10).

The carousel (4) is formed by a single circular part, solidary to the rack (9), supported on central bearings (5), which enables the movement thereof with minimum attrition on a circular path (27), marked at the bottom (21) of the box (20) of the electromechanical device (1). The circular rack (9), jointly with the electric motor (6), reducer (7) and gearing (8) assure the circular gliding of said carousel (4) and, consequently, of the cartridges (3) encased therein.

The carousel (4) is circular in shape with a straight portion (28), projected vertically, forming a series of perimeter housings (29) substantially triangular in shape, formed by side walls (30) and upper prolongation (31), said straight portion (28) being projected vertically linked to the rack (9) by means of appendices (32). Accordingly, the perimeter housings (29) are suitable for adequately receiving the cartridges (3), which are compatible in shape.

Therefore, the perimeter housings (29) and the type of encasement of the cartridge (3) promote a longitudinal freedom of movement in relation to the carousel (4), since the cartridge (3) presents a certain mobility between the side walls (30) and upper prolongation (31). The entrance to the perimeter housing (29) faces the elastomeric header (33) of the cartridges (3).

As soon as it is aligned with the connector nozzle (10), the cartridge (3) is moved by the mechanical actuator (11). The cartridge (3) is advanced by the electric motor (12) which when switched on drives a gearing (13) that activates a straight rack (14), which is displaced forwards or backwards, a drawing cane (15) linked to the cartridge (3) in the direction of the connector nozzle (10). Accordingly, the end of the drawing cane (15) has a recess (34), which is an integral part of the track (35) of the circular path (27), which constitutes a stopper in the lower projection (36) of the cartridge (3).

Therefore, once aligned by the positioning sensor (S), the carousel (4) with the cartridge (3) chosen by the user remains aligned with the connector nozzle (10). The mechanical actuator (11), by means of a drawing cane (15), substantially C-shaped, is displaced in a guide groove (37), at the bottom (21) of the box (20), in the direction of the connector nozzle (10). At its distal end, the drawing cane (15) presents the recess (34), which constitutes a stopper in the lower projection (36) of the cartridge (3), such that the movement of both parts is brought together, that is, if the drawing cane (15) advances towards the connector nozzle (10) the cartridge (3) also advances and vice-versa. It is worth recalling, as already commented upon, that the cartridge (3) is fastened, but with freedom of longitudinal movement, on the carousel (4). When the cartridges (3) are mounted in the reel (9), the lower projections (36) constitute a stopper on the track (35) molded at the bottom (21) of the box (20), which attributes stability and uniform gliding.

After the cartridge (3) has advanced, the forced air flow is made present by the compressor (17). The emission of the aroma begins when the air flow taken in by the compressor (17) in the tears (22) passes through the flexible hose (16), enters the connector nozzle (10) and traverses the inside of the cartridge (3), with the chosen fragrance chosen, already positioned.

The cartridge (3) is mounted in a prismatic triangle shape casing (38), endowed with an elastomeric header (33) which constitutes a valve (39) of a path, represented by converging flexible pallets (40). Internally, the cartridge (3) receives an absorbent cylindrical element (2), which impregnated with a fragrance or aroma, configures a long-lasting scent chamber (41). In the elastomeric header (33), which fits perfectly into the casing (38), in addition to the valve (39) of a path, which is actuated and/or opened when the cartridge (3) enters into the connector nozzle (10), there are also side passages (42), which direct the fragrance or aroma to the upper outlet orifice (43) of the cartridge (3), through which the scent is exhaled.

with the cartridge (3), duly allocated, the mechanical actuator (11) pushes it towards the connector nozzle (10) to the emission position. In a previous step, the air flow takes the flexible hose (16) and the converging flexible pallets (40) of the valve (39) of a path are retracted, giving passage to the air towards the scent chamber (41), already saturated by the fragrance or aroma contained in the absorbent cylindrical element (2). Lastly, the air impregnated with a fragrance or aroma can only escape through the side passages (42) of the elastomeric header (33), which end on the upper outlet orifice (43), through which the fragrance is exhaled. In this position, the cartridge (3) advanced, by way of the elastomeric header (33) force the displacement of the covering pivoting handle (A), of the upper outlet orifice (43) of the cartridge (3) and of the outlet orifice (18) of the top (19), in the sense of releasing both orifices, and with the elastomeric header (33) already inserted into the connector nozzle (10), the aroma or fragrance is released into the environment. As soon as the cartridge (3) is recoiled to maneuvering or turning position, the covering pivoting handle (A) once again seals the outlet orifice (18) of the top (19), the valve (39) of a path also returns and its converging flexible pallets (40) once again seals thus preventing fragrance leakage. When recoiled, the upper outlet orifice (43) is closed by interference with a straight portion (28) of the carousel (4).

To make the change, the user choses the fragrance or aroma to be changed in the application, so that the carousel (4) positions the refill under the recharge port (23) of the cartridges (3), located at the bottom (21) of the box (20) of the electromechanical device (1). The recharge port (23) of the cartridges (3) presents a triangular end where there is a fold (44) which enables by means of a click in an opening (45), having compatible size, located at the bottom (21) of the box (20) where it is pivoted by shaft (46) injected into the part itself. Still on the inner face of the recharge port (23) there are two parallel walls (47) that give continuity to the track (35). Lastly, at the opposite end, a bung (B), which acts in balance in relation to the shaft (46) constitutes a stopper on the recharge port (23) sensor (S2) of the cartridges (3) open, which prevents the carousel (4) from moving in this situation, which would lead to the overlapping of the cartridges (3). In this context, the change is facilitated because the cartridges (3) remain freely positioned inside the perimeter housings (29), it being suffice to open the recharge port (23), remove the empty cartridge (3), and then insert the refill cartridge (3) in the cavity of the housing (29) delimited by the side walls (30) and upper prolongation (31).

Optionally, the electromechanical device (1) may incorporate an autoclean mechanism, which comprises a ring (47), encircling the carousel (4), which has the function of containing the fragrance or aroma in that region. The ring (47) is interconnected by means of hose (48) to an exhaust (49) which, when activated, conducts the air saturated (50) with the aromas or fragrances, from inside the carousel (4), out of the electromechanical device (1). The autoclean is activated whenever the electromechanical device (1) is switched off, or when the user deems necessary. Automatically, the exhaust (49) is activated and forces the entry of clean air (51) from the environment through the opening (52), which enters the inner region of the carousel (4) by a second opening (53), mixing the saturated air (50) following the path already mentioned until it is expelled through the window (54). Autoclean is useful so that the electromechanical device (1), for example, does not impregnate the bag of the demonstrators after testing.

The invention claimed is:

1. A wireless electromechanical device (1) for demonstrating multiple fragrances or aromas formed by a bipartite box (20), comprising a bottom (21) with tears (22) for air intake in a compressor (17), a rechargeable battery (24) provided with energy by external connectors (25), which feeds an electronic circuit (26) and sensors, wherein the fragrances or aromas are contained in an absorbent cylindrical element (2) inserted into an individual cartridge (3), which is interchangeable and encased in a carousel (4) radially moved by an electric motor (6) and a reducer (7) having a shaft containing a gearing (8) which drives a circular rack (9) incorporated to the carousel (4);

wherein the wireless electromechanical device is configured to receive a command via an application, and upon receipt of the command, a mechanical actuator (11) formed by a second electric motor (12), gearing (13) which activates a straight rack (14) drives a drawing cane (15), which pushes, and then retracts the cartridge (3) inside a connector nozzle (10), resulting in an air flow for a flexible hose (16), from where air inflated by the compressor (17) enters the cartridge (3), and forces the emission of the scent by an upper outlet orifice (43) of the cartridge (3) and outlet orifice (18) of the box (20); and a recharge port (23) at the bottom (21) of the wireless electromechanical device (1) enabling changing of the cartridge (3) with a second cartridge.

2. The wireless electromechanical device (1) for demonstrating multiple fragrances or aromas according to claim 1, wherein the motor (6) has a shaft, and wherein positioning of the cartridge (3) in relation to the connector nozzle (10) occurs by means of a positioning sensor (S) located in the shaft of the motor (6) and reducer (7).

3. The wireless electromechanical device (1) for demonstrating multiple fragrances or aromas according to claim 2, wherein the positioning sensor (S) shows the number of turns of the shaft of the motor (6) and reducer (7) with the position of the cartridge (3).

4. The wireless electromechanical device (1) for demonstrating multiple fragrances or aromas according to claim 1, wherein a calibration sensor (S1) places the cartridge (3) in line with the connector nozzle (10) at the start of operation of the electromechanical device (1).

5. The wireless electromechanical device (1) for demonstrating multiple fragrances or aromas according to claim 1, wherein the carousel (4) is supported on central bearings (5) and glides on a circular path (27).

6. The wireless electromechanical device (1) for demonstrating multiple fragrances or aromas according to claim 1, wherein the carousel (4) presents a straight portion (28), projected vertically, forming a series of perimeter housings (29) substantially triangular in shape to receive the cartridge (3) which constitute a stopper on side walls (30) and upper prolongation (31).

7. The wireless electromechanical device (1) for demonstrating multiple fragrances or aromas according to claim 1, wherein the drawing cane (15) of the mechanical actuator (11) moves in a guide groove (37) at the bottom (21) of the box (20); the distal end of the drawing cane (15) presents a recess (34) for setting in a lower projection (36) of the cartridge (3), such that if the drawing cane (15) advances towards the connector nozzle (10), the cartridge (3) also advances and vise versa.

8. The wireless electromechanical device (1) for demonstrating multiple fragrances or aromas according to claim 1, wherein the cartridge (3) is mounted on a prismatic triangular shape casing (38), endowed with an elastomeric header (33) with an entrance that configures a valve (39) of a path, wherein the cartridge (3) has an inside configured to receive an absorbent cylindrical element (2) impregnated with fragrance or aroma, forming a long-lasting scent chamber (41).

9. The wireless electromechanical device (1) for demonstrating multiple fragrances or aromas according to claim 8, wherein the valve (39) has converging flexible pallets (40) of a path, which is actuated and/or open when the cartridge (3) enters into the connector nozzle (10); the elastomeric header (33) has side passages (42), which direct the fragrance or aroma to the upper outlet orifice (43) of the cartridge (3), through which the scent is exhaled.

10. The wireless electromechanical device (1) for demonstrating multiple fragrances or aromas according to claim 7, wherein with the cartridge (3) advanced, the elastomeric header (33) forces the displacement of the covering pivoting handle (A), of the upper outlet orifice (43) of the cartridge (3) and of the outlet orifice (18) of a top (19), in the sense of releasing both orifices, and with the elastomeric header (33) already inserted into the connector nozzle (10), the aroma or fragrance is released into the environment.

11. The wireless electromechanical device (1) for demonstrating multiple fragrances or aromas according to claim 7, wherein with the cartridge (3) recoiled a covering pivoting handle (A) once again seals the outlet orifice (18) of the top (19), a valve (39) of a path also returns and the converging flexible pallets (40) once again seal, preventing fragrance leakage.

12. The wireless electromechanical device (1) for demonstrating multiple fragrances or aromas according to claim 1, wherein by changing the cartridge (3), the user should choose the aroma to be changed in the application, so that the carousel (4) positions a refill under the recharge port (23), located at the bottom (21) of the box (20) of electromechanical device (1).

13. The wireless electromechanical device (1) for demonstrating multiple fragrances or aromas according to claim 12, wherein the recharge port (23) has a triangular end where there is a fold (44) which enables by means of a click in an opening (45); wherein the recharging port (23) pivot by the shaft (46) to inject in the cartridge (3); wherein on an inner face of the recharge port (23) there are two parallel walls (47); at an opposite end to the triangular end where there is a fold (44), a bung (B) constitutes a stopper on a recharge port sensor (S2) of the cartridge (3) open.

14. The wireless electromechanical device (1) for demonstrating multiple fragrances or aromas according to claim 1, wherein the electromechanical device (1) incorporates an autoclean mechanism.

15. The wireless electromechanical device (1) for demonstrating multiple fragrances or aromas according to claim 14, wherein the autoclean mechanism comprises a ring (47), encircling the carousel 4), which has the function of containing the fragrance or aroma in that region; the ring (47) is interconnected, by means of a hose (48), to an exhaust (49) which, when activated, leads air saturated (50) with the aromas or fragrances, from inside the carousel (4), out of the electromechanical device (1) of a window (54).

* * * * *